US006402697B1

(12) United States Patent
Calkins et al.

(10) Patent No.: US 6,402,697 B1
(45) Date of Patent: Jun. 11, 2002

(54) NON-INVASIVE CARDIAC OUTPUT AND PULMONARY FUNCTION MONITORING USING RESPIRED GAS ANALYSIS TECHNIQUES AND PHYSIOLOGICAL MODELING

(75) Inventors: Jerry M. Calkins, Paradise Valley, AZ (US); Tadeusz M. Drzewiecki, Rockville, MD (US)

(73) Assignee: Metasensors, Inc., Rockville, MD (US)

( * ) Notice: Subject to any disclaimer, the term of this patent is extended or adjusted under 35 U.S.C. 154(b) by 0 days.

(21) Appl. No.: 09/488,763

(22) Filed: Jan. 21, 2000

Related U.S. Application Data
(60) Provisional application No. 60/116,648, filed on Jan. 21, 1999, and provisional application No. 60/140,763, filed on Jun. 24, 1999.

(51) Int. Cl.[7] .................................................. A61B 5/08
(52) U.S. Cl. ....................................... 600/532; 600/529
(58) Field of Search ................................. 600/529, 531, 600/532, 533, 538, 537

(56) References Cited
U.S. PATENT DOCUMENTS

| | | | |
|---|---|---|---|
| 3,896,792 A | | 7/1975 | Vail et al. |
| 4,966,141 A | | 10/1990 | Bacaner et al. |
| 5,836,300 A | | 11/1998 | Mault |
| 5,971,934 A | * | 10/1999 | Scherer et al. ............. 600/532 |
| 6,059,732 A | * | 5/2000 | Orr et al. .................... 600/532 |
| 6,106,480 A | * | 8/2000 | Gam De Abreu et al. .. 600/532 |
| 6,135,107 A | * | 10/2000 | Mault ......................... 600/532 |
| 6,251,082 B1 | * | 6/2001 | Rayburn ..................... 600/532 |

OTHER PUBLICATIONS

Kim et al., "Estimation of True Venous and Arterial PCO$_2$ By Gas Analysis of a Single Breath", J. Appl. Physiol., vol. 21, No. 4, pp. 1338–1344 (1966).
Fletcher et al., "Deadspace and the Single Breath Test for Carbon Dioxide During Anesthesia and Artificial Ventilation" Br. J. Anaesth., vol. 56, pp. 109–119 (1984); and.
"Fick Techniques", Enc. of Med. Devices and Instr., Wester, J.D., Wiley, NY, pp. 1302–1314 (1988).

* cited by examiner

Primary Examiner—Kevin Shaver
Assistant Examiner—Navin Natnithithadha

(57) ABSTRACT

A cardiac output monitoring system (10) includes a respiratory flowmeter (14) and a gas analyzer (20, 22) capable of determining cardiac output on a breath-by-breath basis by non-invasively measuring properties of respiratory gasses and applying the Fick principle. The gas analyzer has the capability to simultaneously quantify multiple gas concentrations, including inhaled and end-tidal concentrations of any constituent of respiratory gas mixtures of a known number of possible constituents, in real time on a breath-by-breath basis, by measuring independent properties of the mixture. The respiratory flowmeter determines the volumetric and mass flow rates of any gas/gasses as calculated from the product of measured total respiratory flow and the measured volumetric concentration in real time on a breath-by-breath basis. From these measurements, cardiac output can be determined on a breath-by-breath basis by applying appropriate numerical algorithms based on the Fick principal, including corrections for physiological conditions such as shunts and deadspace.

21 Claims, 11 Drawing Sheets

NON-INVASIVE CARDIAC OUTPUT AND PULMONARY FUNCTION MONITORING USING RESPIRED GAS ANALYSIS TECHNIQUES AND PHYSIOLOGICAL MODELING

CROSS REFERENCE TO RELATED APPLICATIONS

This application claims priority from U.S. Provisional Patent Application Serial No. 60/116,648 entitled "Non-Invasive Cardiac Output Monitor Using Respired Gas Analysis Techniques And Physiological Modeling", filed Jan. 21, 1999, and from U.S. Provisional Patent Application Serial No. 60/140,763 entitled "Non-Invasive Cardiac Output and Pulmonary Function Monitoring Using Respired Gas Analysis Techniques And Physiological Modeling", filed Jun. 24, 1999. The disclosures of these provisional applications are incorporated herein by reference in their entireties.

BACKGROUND OF THE INVENTION

1. Field of the Invention

The present invention relates to methods and apparatus for determining cardiac output, the amount of blood the heart is pumping, as well as identifying pulmonary functions, without resorting to invasive techniques which introduce foreign objects and the like, into a body.

2. Description of the Related Art

Monitoring the cardiovascular system to determine myocardial performance is of paramount importance in patient care, regardless of whether the patient is located in the physician's office, emergency or operating room, intensive care unit, at an accident scene or in transit (e.g., in an ambulance). Although routine cardiac monitoring usually begins with a determination of the patient's heart/pulse rate and blood pressure, in the case of patients who are experiencing cardiac difficulties or distress, additional diagnostic details regarding the operation of the heart are needed. Such additional monitoring may quickly progress to include an electrocardiogram (EKG) and the measurement of hemodynamic variables such as cardiac output.

The term cardiac output is defined as the mean or average total blood flow in the circulatory system per unit time. Cardiac output is associated with the strength of the heart and is consequently an important parameter in assessing the condition of a patient's health. Knowledge of cardiac output level and trends have important diagnostic value in that they provide the clinician with information to help him/her assess how well the myocardium is functioning so as to provide the basis for the timely delivery and prescription of appropriate therapeutic modalities. Pulmonary function relates to the ability of the body to make use of oxygen and to eliminate wastes such as carbon dioxide. This parameter is strongly affected by physiological conditions such as deadspace and shunts, and the ability to quantify these conditions forms a major part of cardiopulmonary therapy.

Owing to the uncertainties of the geometry of blood vessels (e.g., diameter, compliance, etc.) and the dynamic nature of the heart itself, conventional flowmetering techniques such as flow resistance measurement or velocity (e.g., Doppler and ultrasonic) measurements have proven unreliable in estimating cardiac output. As a result, cardiac output is routinely measured invasively; that is, by surgically placing an instrument into the arteries near the heart.

The current state-of-the-art, and arguably the "gold standard" for cardiac output measurement, is considered to be either the Direct Fick or thermodilution technique using a flow-directed catheter (Swan-Ganz catheter). The catheter is physically threaded through a large vein (femoral, internal jugular, etc.) into and through the right atrium and right ventricle of the heart into the pulmonary artery located between the heart and the lungs. At that point, thermal dilution techniques may be used to quantify the blood flow. Unfortunately, because of the invasive nature of the technique, the potential risk to the patient of hemorrhage, dysrhythmia or cardiac arrest is relatively high. Consequently, the routine use of invasive techniques such as thermal dilution to measure cardiac output is presently limited to specific clinical situations where the benefits far outweigh the risks.

A significant number of patients (as many as two percent) do not survive the surgery associated with the catheter insertion procedure itself. Hence, this technique is limited to those situations where patients are extremely ill and the increased risk for increased morbidity and mortality is acceptable. Efficacy studies in recent medical literature report data that raises questions as to the risk-benefit ratio of the information provided by invasive cardiac output measurement and whether invasive cardiac output measurement is in the best interest of the patient. In addition to the intrinsic danger of the invasive procedure, the monetary cost of the procedure is relatively high, as it is in itself a surgical procedure and, as with almost all surgical procedures, its hands-on labor intensity by expensive medical personnel results in high costs. It is estimated that nearly $200 million is spent in the U.S. alone for invasive cardiac procedures, equipment and materials, and recent medical literature also questions the cost effectiveness of these invasive techniques.

Adding to the increasing concern that the cost-benefit ratios may not be in the patient's best interest is the fact that many patients may not be adequately monitored and consequently are being put at risk from lack of diagnostic information. Presently, no reliable, accepted, cost-effective, non-invasive techniques are available for continuous monitoring; thus, only the sickest and highest risk patients are candidates for continuous cardiac monitoring. This leaves a huge population that goes unmonitored, of which it is well known that significant numbers encounter cardiac distress of one kind or another during non-cardiac-related procedures. There are many clinical situations such as most routine surgery/anesthesia, outpatient care, emergency medicine, and home care where monitoring cardiac output is not routine, but if it were, would be of significant benefit to patient care. There are significant complications that require treatment, many of which may have been prevented had myocardial function monitoring been available and appropriate responses initiated. Current estimates of the costs of aftercare treatment for such cardiac complications exceed $22 billion in the U.S. alone.

Non-invasive and less invasive techniques are therefore highly desirable. Unfortunately, because of the variability and complexity of the physiology of the circulatory system and the pathology of disease, no currently used non-invasive or less-invasive methodologies are known to be capable of obtaining reliable cardiac output values. Although less-invasive methodologies such as impedance cardiography, Doppler-shift techniques, and non-invasive rebreathing and single-breath Fick techniques are or have been available commercially to measure cardiac output, in their current implementations, they all suffer from significant problems and/or disadvantages. In general, all of these techniques are extremely expensive, require a highly trained technical staff, and are limited to a few well-defined clinical situations. In addition, each technique has unique specific limitations.

More particularly, impedance cardiography requires the correct placement of electrodes on the neck and abdomen that are excited by a high frequency (e.g., 100 kHz) current and the subsequent monitoring of the resulting impedance changes between the electrodes. The impedance changes of the chest are used to determine the cardiac stroke volume resulting from the expansion and contraction of the cardiac volume. Cardiac output can be calculated by combining this volume with heart rate in an appropriate algorithm. The limitations of this technique include: the need/ability to correctly place the electrodes, accurate accounting for the volume changes resulting from the inhalation and exhalation of the lungs, and patient movement. Furthermore, the high impedance electrodes act as antennas that pick up considerable amounts of electromagnetic interference (EMI), thereby interfering with the measurements.

The Doppler-shift technique is based on the effect of the shift in frequency of sound from a stationary source that is reflected by a moving object. With this method, the average velocity of the blood flowing in an artery can be readily measured. However, to determine the volumetric flowrate, the cross-sectional area of the artery must be known. Obviously, soft tissue visualization techniques such as MRI are not practical at this time for general use, and ultrasound imaging generally tends not to be accurate enough, although it is used to provide a relative measure in some applications such as transesophageal-echocardiography. Costs are prohibitively high, and in this age of managed care cannot be considered practical for routine use. Esophageal Doppler techniques are also plagued with inevitable patient motion artifacts.

A variety of indirect Fick techniques, including breath holding, single breath and rebreathing, have been proposed over the years to estimate cardiac output from various measurements of respired and tracer gasses. Breath holding and single-breath techniques using tracer gasses have had limited success but are not suited to continuous monitoring. A single-breath technique proposed by Kim et al. in "Estimation of true venous and arterial $PCO_2$ By Gas Analysis of a Single Breath," J. Appl. Physiol., Vol. 21, No. 4, pp. 1338–1344, (1966), incorporated herein by reference in its entirety, probably had the greatest potential because of the promise of breath-by-breath monitoring. However, general acceptance has been lacking due to technology limitations for precise, real time, simultaneous respiratory gas measurements and limited experimental validation of their underlying assumptions.

Perhaps most popular and most widely accepted of the indirect Fick techniques have been $CO_2$ rebreathing techniques. Presently, the only commercially available non-invasive device is the Novametrix Non-Invasive Cardiac Output (NICO) monitor, which monitors respired carbon dioxide production combined with partial rebreathing (inhaling air with elevated carbon dioxide levels) in a variation on the well-known Fick Principle. (The Fick Principle relates essentially to a statement of flow continuity and mass balance over the cardiovascular system.) More specifically, a non-dispersive infrared $CO_2$ sensor and a venturi-type flowmeter measure the $CO_2$ concentration and respired volumetric flowrate and hence $CO_2$ production. The Fick equation is used to calculate cardiac output as the ratio of the carbon dioxide produced to the arteriovenous difference of carbon dioxide content in blood. NICO is reported to have reasonable correlation with direct Fick and indicator dilution measurements in patients with normal, healthy lungs with minimal deadspace and/or no pulmonary shunts.

However, the NICO system's reliance on the products of metabolism (i.e., the Novametrix sensors can measure only carbon dioxide) results in questionable accuracy in the presence of shunts and deadspace in the lungs; the accuracy of the NICO system is also compromised because it must rely on compensatory algorithms that are highly dependent on physiological conditions and unknown metabolic and respiratory parameters. Consequently, results are poor for patients with pulmonary and/or obstructive airway disease due to the effects of V/Q mismatching caused by increased pulmonary shunts and deadspace. These effects invalidate the assumption that $P_eCO_2$ can be used to approximate the values for $P_vCO_2$ and $P_aCO_2$. The dilutional effects of a significant shunt on the pulmonary capillary blood flow invalidate the assumption that systemic cardiac output is equal to pulmonary capillary blood flow. Reasonable success has been achieved in compensating for shunts by measuring the degree of $O_2$ saturation in a peripheral artery with a pulse oximeter. The major disadvantages of this technique are: bulk of the rebreathing apparatus and the time required to collect the data to calculate cardiac output. This latter disadvantage precludes the use of this device for continuous, or even breath-by-breath monitoring; consequently, dynamic changes may not be detected quickly enough for preventive measures to be taken. Furthermore, since the rebreathing may take longer than a recirculation time, readings may be affected by accumulated $CO_2$.

While monitors for the continuous, breath-by-breath, measurement of $CO_2$, $O_2$, and anesthetic agents are commercially available, all are lacking in one or all of the following attributes: reliability, ease of operation, accuracy, the need for calibration, small size, and low acquisition cost and life-cycle cost. For example, $CO_2$ monitors using non-dispersive IR spectroscopy can cost over $1000 for hand-held versions and as much as $20,000 (with additional high life-cycle costs associated with the periodic calibration and maintenance of the equipment) for a full-spectrum operating room gas monitoring. Mass spectroscopy and Raman scattering systems are even more costly and bulky. In addition to cost, physical size, and inconvenience of operation (calibration) conventional systems have found limited use of gas monitoring in the field for such things as validation of endotracheal (ET) tube placement during emergency intubation and patient transport. Extubation, leading to severe, irreversible consequences, frequently occurs during patient transport, yet no monitors meeting the above characteristics have been available.

Consequently, there remains a need for a reliable, cost-effective, non-invasive cardiac output monitoring system capable of continuously measuring cardiac output and pulmonary function on a breath-by-breath basis using measurements of inspired and respired gasses. The availability of cardiac output measurement to routinely monitor the large population currently without benefit of such monitoring could significantly reduce the huge aftercare costs and morbidity and mortality resulting from undiagnosed cardiac complications in non-cardiac-related procedures. A lightweight, rugged device would be ideally suited for use in field environments such as the ambulance and MEDEVAC transport, as well as the doctor's office, clinic, emergency and operating rooms and in intensive care units (ICU).

Since there is no currently acceptable noninvasive cardiac output monitor available for routine use, there remains a need for a technique to accurately measure cardiac output and eliminate risk of infection or invasive trauma to the patient. Further, any technique that is economical, reliable, accurate, and simple to operate and maintain becomes a candidate for routine utilization. Moreover, a device that is lightweight and small, opens the market to ambulatory monitoring, sports and physical fitness, and home care of cardiac patients. Finally, such a device would complement rural and military telemedicine where remotely located specialists can diagnose and treat patients given sufficient patient data.

SUMMARY OF THE INVENTION

Therefore, in light of the above, and for other reasons that become apparent when the invention is fully described, an object of the present invention is to provide a non-invasive cardiac output monitoring system that uses measurements of inspired and respired gasses in the determination of cardiac output.

It is another object of the present invention to utilize a mathematical model of the human physiology that will compensate for variations in physical and disease states in determining cardiac output from respired gasses.

It is a further object of the present invention to measure uptake and release of inert and/or insoluble indicator gasses that are not metabolized and absorbed in order to eliminate the vagaries of the metabolic and absorption processes in determining cardiac output.

It is yet a further object of the present invention to use a gas analyzer that measures or assays all the gasses that are inhaled and respired, not just an indicator gas alone, thereby allowing for a complete description of the uptake, distribution and release of the gasses, that then allows for accurate inputs to the physiological model.

It is still a further object of the present invention to provide for a very low cost implementation of the technology in order to promote widespread use and to improve the general standards of care for patients.

It is another object of the present invention to measure, in a real time, breath-by-breath situation, oxygen and carbon dioxide concentration from which both mixed venous and arterial concentrations of carbon dioxide can be determined.

Another object of the present invention is to measure on a real time, breath-by-breath basis the anatomical and physiological deadspace of the lungs by combining breathing mass flow measurement with concentration waveform analysis.

Still another object of the present invention is to provide a low cost means for determining the cardiac output and pulmonary function of a human being on a breath-by-breath basis while accurately accounting for disease states as well as physical conditions.

Yet another object of the present invention is to provide a cardiac output monitoring device that measures attributes of respired gasses on a breath-by-breath basis, which measurements can be used with any of the known Fick techniques for determining cardiac output non-invasively.

A fundamental aspect of the present invention is the use of a respired gas analyzer that is capable of simultaneously quantifying the concentrations of several gasses in real time and a true, real time mass flowmeter to calculate uptake, production and expiration of gasses to provide measurements with known relationships to cardiac output and pulmonary function. A gas analyzer suitable for use in the present invention is disclosed in pending U.S. patent application Ser. No. 09/104,997 entitled "Method and Apparatus For Real Time Gas Analysis" filed Jun. 26, 1998 by Tadeusz M. Drzewiecki, and a pending provisional U.S. patent application Ser. No. 60/121,370 entitled "Methods and Apparatus for Real Time Fluid Analysis" filed Feb. 25, 1999 by the same inventor. The subject matter disclosed in those applications is incorporated herein by reference in its entirety.

The combination of a real time mass flowmeter and an inexpensive gas analyzer capable of simultaneously determining concentrations of multiple gasses in real time permits for the first time accurate determination of cardiac output on a breath-by-breath basis from analysis of respired gasses. More particularly, the cardiac output monitoring system of the present invention can be used with any of the Fick-principle-based non-invasive techniques that have been proposed in the art for measuring cardiac output from respired gasses, but that have heretofore been impractical, prohibitively expensive, inaccurate and/or unreliable. Moreover, the parameters measured and the extensive information provided in real time by the cardiac output monitoring system of the present invention allow known techniques to be refined and extended to more accurately account for pulmonary factors such as shunts and deadspace in the determination of cardiac output.

The gas analyzer disclosed in the aforementioned Drzewiecki patent applications simultaneously and in real time assays gasses, allowing accurate quantification of all the constituents of respiratory gas mixtures. Because the gas analyzer measures physical properties of a gas mixture, including density and viscosity, a conventional flowmeter can be compensated for changes in gas properties, not only as a function of temperature but also for changes in composition. This allows the use of any one of a variety of low cost pressure-drop-type (fixed or variable orifice) flowmeters to accurately measure respired flows over a wide range of gas compositions, with equivalent accuracy of expensive mass flowmeters. Thus, artifacts caused by breathing in products of combustion or other gasses (e.g., anesthetics) that would affect the computation of gas uptake/production by giving erroneous volumetric or mass flows are eliminated. In this manner, the volumetric gain or loss from the lungs can be quantified throughout the respiratory cycle to provide the necessary data to accurately calculate cardiac output using the Fick Principle. By overcoming the technical difficulty of measuring the concentrations of oxygen and carbon dioxide simultaneously (with standard errors that cancel rather than add as they do with independent sensors) an accurate measure of cardiac output can be obtained using single-breath techniques, such as that disclosed by Kim. Furthermore, by providing an improved methodology for estimating alveolar $CO_2$ and $O_2$ concentration values that includes the effects of physiological (including alveolar) deadspace, by using the Bohr equation combined with the considerable work of Fletcher on analyzing $CO_2$-volume waveforms, in combination with an iterative anatomical/physiological model of gas exchange that converges on measured expiratory gas concentrations, the Kim technique provides accurate results under significantly broader conditions to include exercise and disease states. Finally, by including a pulse oximeter to measure $O_2$ saturation, pulmonary shunts can be compensated for directly in the expression derived for the $O_2$ tension rather than by trying to estimate a value for shunts directly and thereby adjust the $CO_2$ values.

The cardiac output monitor of the present invention poses essentially no risk to the patient, is easy to use, is inexpensive to manufacture and has virtually no low life-cycle costs (e.g., no recalibration is ever required), thereby making it economical to operate, and can be sized and packaged to be handheld while maintaining an instrument (e.g., waveforms, etc.) level output capability.

By measuring physical properties such as density, viscosity and specific heat with very simple but highly precise pressure, flow, temperature and frequency transducers, the assay of the constituent concentrations is precisely calculated. The unique combination of concentrations that make up a gas mixture with given measured properties (viscosity, density, specific heat) is determined by deconvolving the fundamental relationships that define mixture property values in terms of their constituent concentrations. State-of-the-art, low cost, ultra-high dynamic range, microelectromechanical system (MEMS) pressure transducers, and a highly precise platinum RTD temperature sensor integrated with a specially designed fluidic oscillator flowmeter, measure the pressure drop, temperature and flow in a microfluidic capillary viscometer, orifice densitometer, and sonic microcalorimeter (specific heat sensor) integrated on a precision micro-injection molded Laboratory-on-a-Chip (LOAC). A high-speed microprocessor provides solutions to the governing equations and drives an LCD. Because the concentrations are determined from physical first principles, the gas analyzer never requires calibration or maintenance, which is a major advantage for field-use devices.

According to one embodiment of the present invention, a known amount of an essentially inert, insoluble, indicator gas is tracked during respiration. The input parameters (cardiac output, deadspace, shunts) to a validated physiological model (software) are iterated to obtain a matching time-history of the released (exhaled) indicator gas. The use of a model that allows for individual variations and disease states, as well as variations in body mass and uptake and distribution parameters, results in a credible as well as accurate output, that, because it matches the measured values, represents a reasonable estimate of the parameters. The values of cardiac output, shunts and deadspace that match the measured values are thus among the outputs of the monitoring system of the present invention.

In another, more general embodiment of the present invention, the use of a tracer gas is dispensed with and the analysis of the consumed oxygen and produced carbon dioxide and their concentration waveforms is used to provide a measure of the mixed venous and arterial concentrations of carbon dioxide and a measure of the anatomical and physiological deadspace, leaving the physiological model to be used only to correct for and measure pulmonary shunts corresponding to a particular disease state.

The low cost, affordable, accurate respired gas analysis technology that constitutes the basis of the present invention provides a mechanism for determining the concentrations of the constituents of a gas mixture by measurement of certain independent physical and/or thermodynamic properties such as density, viscosity, specific heat, dielectric constant, refractive index, electromagnetic radiation absorptivity, etc., of the mixture and determining the assay of the mixture that produces the measured values of the mixture properties. This technology, when applied to the measurement of cardiac output, offers significant cost and diagnostic advantages over other technologies that utilize the well-known and accepted Fick principle. For example, currently available non-invasive methods (e.g., the aforementioned NICO system) are limited to the use of only one indicator gas (carbon dioxide or oxygen) at a time. Since these gasses are products of metabolism or are themselves metabolized, the algorithms used are necessarily complex and not well validated because they must be able to accurately consider the metabolism process. By being able to use essentially inert (non-metabolizing) gasses, nitrogen and/or anesthetic gasses may be used as indicators and, moreover, the presence of more than one can be monitored simultaneously. This enables the clinician to select the indicator(s), or combinations thereof, appropriate to a particular clinical situation.

For example, a denitrogenated patient on pure oxygen (and anesthetic gasses) in the operating room (OR) is a good candidate for a nitrogen indicator, whereas, a patient in the intensive care unit (ICU), who is breathing air or air and oxygen, may be a candidate for an anesthetic agent or another inert indicator such as helium. By choosing indicators that are not present in the body, the problem of accounting for residual indicator is eliminated. That is, one may account for all of the indicator injected as it is released and exhaled.

The above and still further objects, features and advantages of the present invention will become apparent upon consideration of the following definitions, descriptions and descriptive figures of specific embodiments thereof wherein like reference numerals in the various figures are utilized to designate like components. While these descriptions go into specific details of the invention, it should be understood that variations may and do exist and would be apparent to those skilled in the art based on the descriptions herein.

DESCRIPTION OF THE PREFERRED EMBODIMENTS

Figure 1:
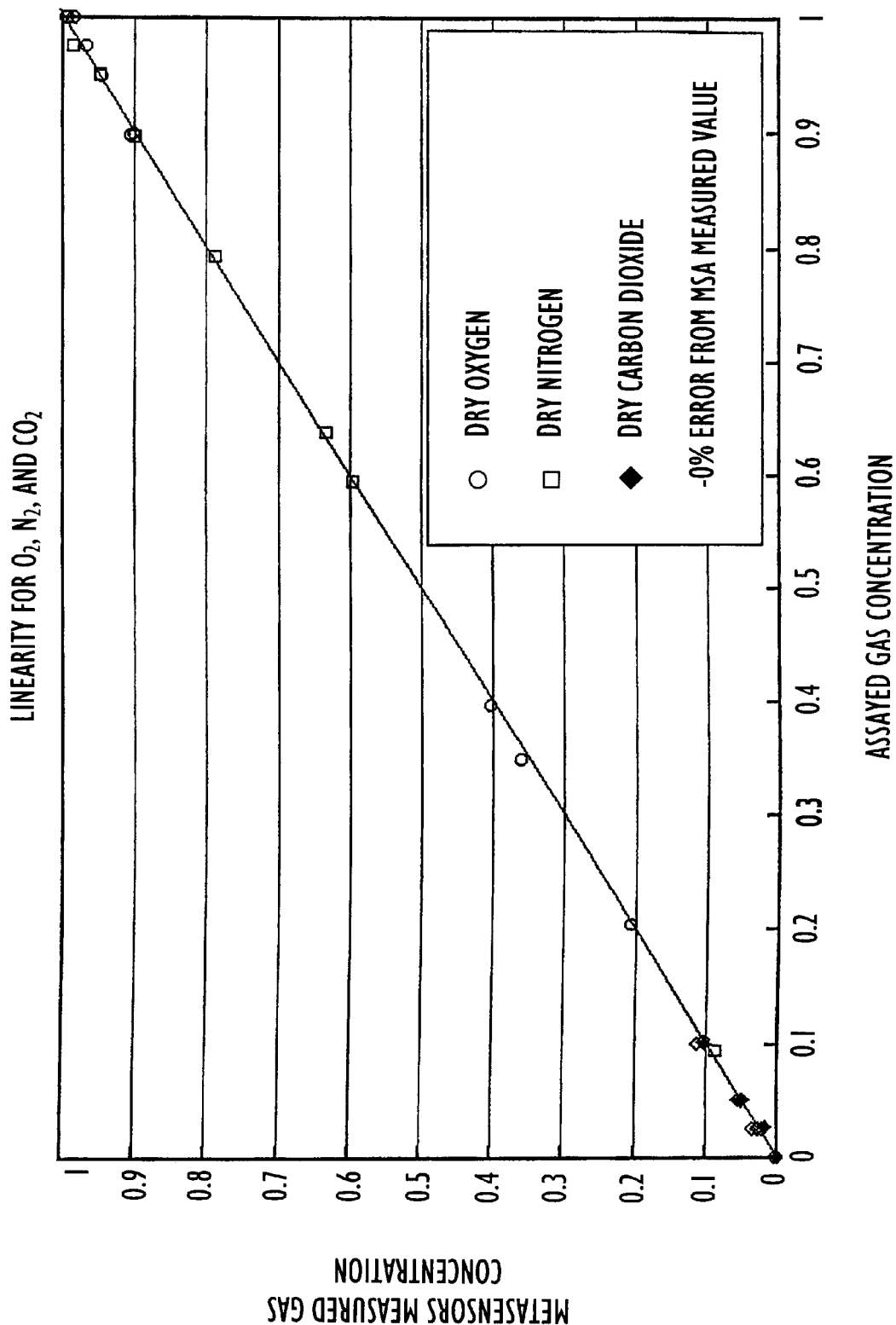
FIG. 1 is a graph showing the linearity and accuracy of the gas analyzer of the cardiac output monitor of the present invention over a range of $O_2$, $N_2$, and $CO_2$ and concentrations.
Figure 2:
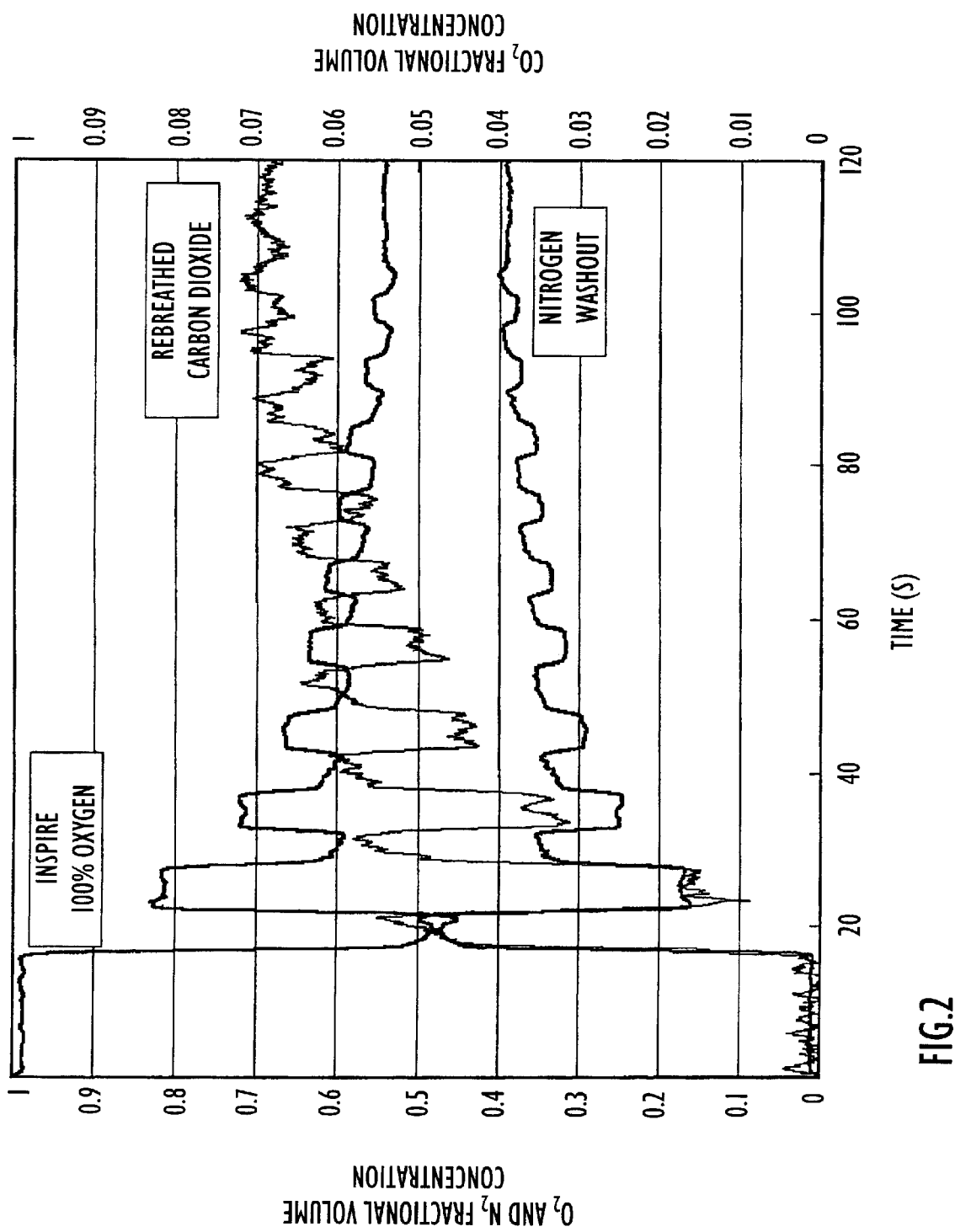
FIG. 2 is a graph depicting typical measurements of rebreathed $O_2$, $N_2$, and $CO_2$ measured by the gas analyzer of the cardiac output monitor of the present invention.

The following detailed explanations of FIGS. 1–11 and of the preferred embodiments reveal the method and apparatus of the present invention.

The main components of the cardiac output monitor of the present invention are: a low-cost respiratory gas analyzer, a respiratory gas flowmeter, and the appropriate numerical algorithms necessary to make the calculations of cardiac output and the physiological corrections. The multiple medical gas respiratory gas analyzer, examples of which are disclosed in the aforementioned Drzewiecki patent applications, has the capability to quantify gas concentrations, including inhaled and end-tidal concentrations (approximating arterial and mixed venous blood partial pressures), of any constituent of respiratory gas mixtures of a known number of possible constituents, in real time on a breath-by-breath basis. A respiratory flowmeter, described hereinbelow, accurately determines the volumetric and mass flow rates of any gas/gasses as calculated from the product of measured total respiratory flow and the measured volumetric concentration. With this flowmeter, the resulting inhaled/exhaled volumes of the respiratory gas mixture are quantified in real time on a breath-by-breath basis.

The gas analyzer of the cardiac output monitoring system of the present invention can determine in real time the individual concentrations of fluid constituents in a mixture of N fluids by measuring independent properties of the mixture. In particular, N equations that, from first principles, relate the individual fluid concentrations to measured properties of the mixture, are solved for the N unknown individual concentrations of the fluids in the mixture. N−1 properties of the mixture are measured by N−1 sensors, which from cost considerations are preferably fluidic sensors, but may be any other technology devices, and N−1 of the N equations are formed from the determined properties. The Nth equation is the constitutive equation which requires that the sum of the unknown concentrations of the N known constituents be equal to unity.

For example, as described in greater detail in the aforementioned Drzewiecki patent applications, the individual concentrations of four gasses in a mixture of four known gasses can be determined by measuring the ambient pressure, temperature and flow rate of the sample flow of the mixture, the subsequent pressure drop of the mixture sample flow across a capillary and across an orifice which may be the supply nozzle of the flowmeter oscillator, and finally the acoustic velocity in the mixture. The sample flow rate can be measured by passing the flow through a fluidic feedback oscillator and measuring the output frequency period which is proportional to transit time. The acoustic velocity can be measured using a sonic oscillator. From these measurements, the density, viscosity and specific heat of the mixture are computed, and the four unknown concentrations of the four known gasses are determined by solving in real time four independent equations (i.e., an equation relating mixture density to the concentrations, an equation relating mixture viscosity to the concentrations, an equation relating mixture specific heat to concentrations, and the constitutive equation).

Preferably, the oscillator flowmeter, sonic oscillator and the capillary are formed as a disposable sensor module comprising a single small, thin, plastic lamination. By attaching (in a separable manner) pressure and temperature sensors at appropriate points, all necessary measurements can be performed. Any one of the oscillator nozzles can serve as the orifice, thereby eliminating the need for a separate orifice. The disposable sensor module is connected via a separable interface to a replaceable transducer module containing the transducers and amplifiers used to measure the characteristics of the mixture, as well as containing the vacuum line for drawing a sample.

Advantageously, low cost, fluidic sensors measure the flow, density, viscosity and speed of sound in gas mixtures. Low-cost micro-electro-mechanical systems (MEMS)-based electronic pressure transducers, low-cost integrated circuit temperature transducers, and ultra-low cost piezo-electric film microphones provide electronic inputs to a microprocessor. The gas analyzer of the present invention requires no user calibration or maintenance and may be integrated into existing monitoring systems. For example, the gas analyzer can be added along the same flow path as other sensors or can be added in a separate flow path.

Although fluidic sensors are preferable for the aforementioned reasons, the gas analyzer can be implemented with other types of sensors. For example, piezo-electrically-driven surface acoustic wave (SAW) devices have been used to determine density and speed of sound, ultrasonic devices can density, and electrochemical devices can measure viscosity. Depending on their relative cost and accuracy advantages, these devices may be advantageously used in place of fluidic sensors.

One of the important advantages of the gas analyzer of present invention is the ability to simultaneously determine the individual concentrations of N gasses in a mixture of N known gasses by using inexpensive sensors to measure properties of the mixture as a whole and by solving N independent equations relating to the properties of the mixture. The number of gasses whose individual concentrations can be determined can be increased by incorporating into the gas analyzer additional sensors that measure additional independent properties of the mixture as a whole. If additional properties of the mixture can be independently measured by any means and related to unknown concentrations, concentrations of additional gasses can be determined. In general, if N−1 independent properties of the mixture of gasses can be measured, then N equations can be developed and solved for N gas concentrations (the Nth equation being the constitutive equation).

Operation of the gas analyzer of the cardiac output monitor of the present invention has been experimentally verified. On a dry gas basis, a patient exhales a mixture of $O_2$, $CO_2$ and enriched $N_2$ (a fixed mix of $N_2$, $CH_4$, Ar, and trace gasses). A very low sidestream flow (~40 ml/min) sensor comprising a capillary viscometer and an orifice densitometer has demonstrated analysis accuracy of better than ±0.5 vol %, with a resolution of less than ±0.25 vol %, for $CO_2$ and $O_2$. FIG. 1 shows the accuracy and linearity that is inherent to this device from tests using twelve randomly selected known-assay mixtures of $O_2$, $CO_2$ and $N_2$. Analysis accuracy and resolution for gasses with significantly different physical properties, such as the volatile inhalation anesthetic agents Halothane and Isoflurane, in mixtures of $O_2$, $CO_2$ is ±0.05 vol % with a resolution of less than 200 ppm. Response is real time ($T_{90}$<200 ms). Typical responsivity is evidenced by the capability to measure breathing in real time. Typical of this is the record of a rebreathing procedure shown in FIG. 2. Starting with pure $O_2$ the $O_2$ decreases as $CO_2$ concentration increases, and $N_2$ increases as the tissues excrete $N_2$ during denitrogenization. (Note that $CO_2$ does not equilibrate probably because recirculation adds to the venous level.)

Experimental results indicate that the gas analyzer provides assays of $CO_2$ and anesthetic agents with resolution and accuracy comparable to those of IR devices, assays of $O_2$ that are significantly more accurate than that of fuel cell, paramagnetic and Clark electrode $O_2$ sensors, and assays of $N_2$ that are superior to Raman systems. Also, with the exception of mass spectroscopy and Raman scattering, this gas analyzer is the first to offer real time quantification of nitrogen, which can be a valuable safety feature in the operating room by detecting breathing circuit leaks and disconnections, as well as air emboli.

In addition to gas concentrations, which can be calculated using the aforementioned gas analyzer, a determination of cardiac output from respired gasses using a Fick-based technique typically involves a determination of the respired flow rate. For example, certain Fick techniques require the accurate quantification of both oxygen consumption and carbon dioxide production. The rate of consumption, or production, is the product of the instantaneous concentration and the flow rate. Measurement of respired flow rate (pneumotachometry) is conventionally made with one of a variety of devices: turbine meters, rotometers, fixed or variable orifices, capillaries, hot wire/film anemometers, ultrasonic/acoustic transit time sensors, etc. With the exception of ultrasonic/acoustic devices, the accuracy of the flow through a fixed (nozzle, venturi) of variable (rotometer, flap) orifice depends on an intimate knowledge of, primarily, density as noted in the Bernoulli orifice equation, $$\Delta P = \rho Q^2 / (c_d^2 A^2) \tag{1}$$

where $\Delta P$ is the pressure drop, $\rho$ is the density, Q is the volumetric flow, $c_d$ is the discharge coefficient (which typically is viscosity dependent) and A is the cross-sectional area. (A similar density-dependent equation can be derived for turbine meters where the density dependence comes from the conversion of the fluid kinetic energy to motion of the moving part/vane.)

Figure 3:
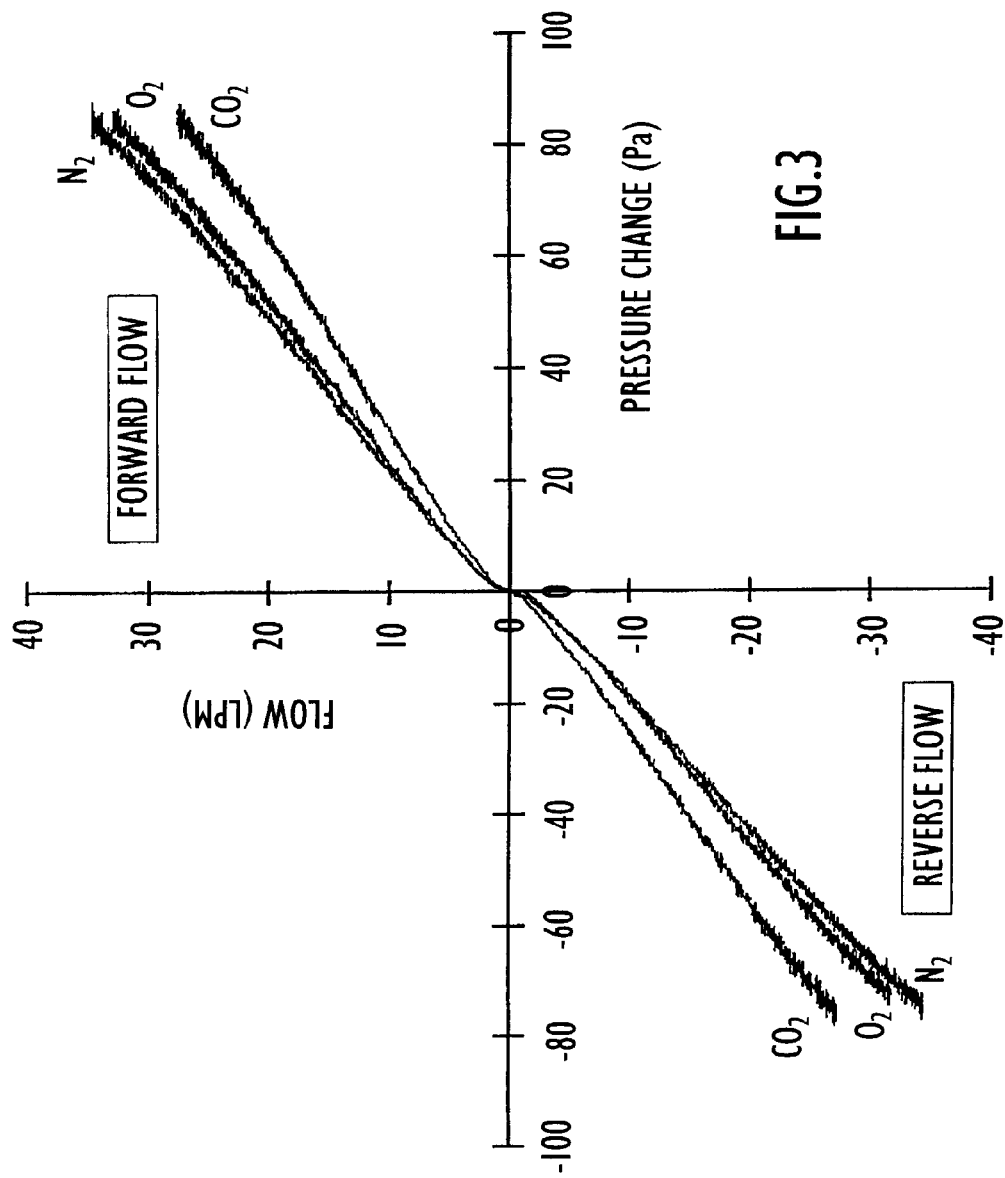
FIG. 3 is a graph showing the Hamilton respiratory flowmeter pressure-flow relationship as a function of density for $O_2$, $N_2$, and $CO_2$.

Since the gas analyzer of the present invention measures density and viscosity of the respired gas, a very low cost flowmeter, such as a bidirectional Hamilton variable area orifice device can be used to accurately compute Q because density is inherently known. The pressure-flow relationship for this device for the three constituent gasses in air (nitrogen, oxygen, and carbon dioxide), is shown in FIG. 3 which clearly demonstrates the device's density dependence (e.g., high density $CO_2$ has lowest flow at the same pressure drop) and the error incurred if density is unknown. The pressure-flow relationship for this device, where the area is a function of the pressure drop via the displacement of a wedge-shaped flap can be shown to be:

$$Q^2 = [L^2 / 2 A_F^2 k^2 \rho] [\Delta P^3 - \Delta P^5 / 4 A_F^2 k^2 L^2] \tag{2}$$

where L is the characteristic dimension of the flap, $A_F$ is the area of the moving flap and k is the effective spring constant of the cantilevered flap, and $\rho$, again, is the density.

Given the accurate determination of volumetric flow, the product of the flow, Q, with the individual gas concentrations during the exhaled breath gives $CO_2$ production and $O_2$ consumption, the ratio of which is respiratory quotient, R, a term that is critical in the determination of cardiac output, as detailed hereinbelow.

Figure 4:
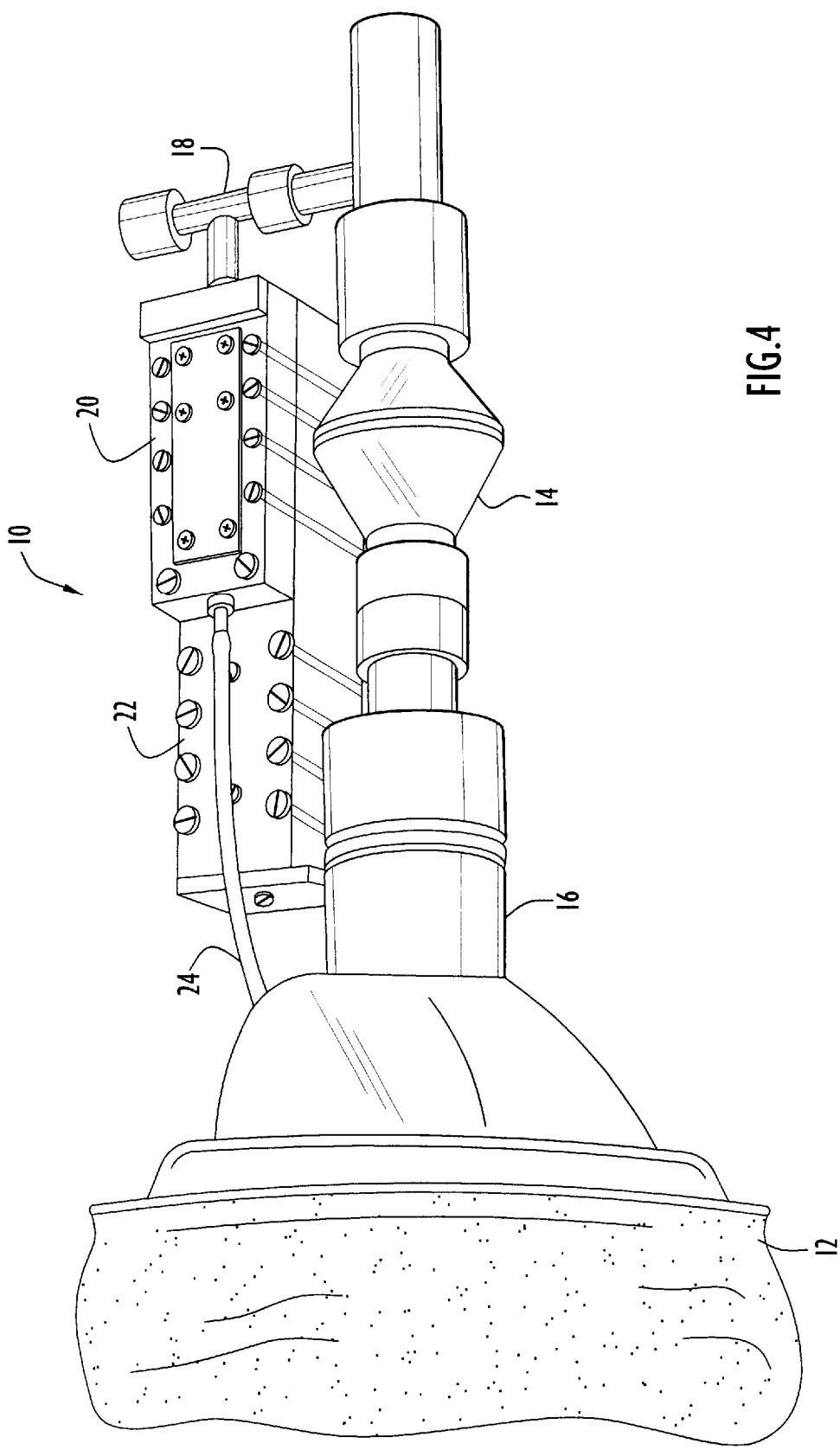
FIG. 4 is perspective view of an experimental (breadboard) metabolic sensor used measure cardiac output in accordance with the present invention.

FIG. 4 illustrates an experimental cardiac output monitor 10 constructed to demonstrate the feasibility of readily acquiring the data required to implement the methodologies of the present invention. Cardiac output monitor 10 includes a face mask 12 for receiving respired gasses from a subject. A respiratory flowmeter 14, coupled to the face mask via a humivent 16, measures the volumetric respiratory flow. A sample port 18 at the output of flowmeter 16 provides a sample flow to the gas analyzer. The gas analyzer includes a gas sensor 20 containing, for example, the aforementioned fluidic sensors for measuring properties of the sample gas, and a transducer module 22. A vacuum line 24 draws the sample gas through the gas sensor 20 of the gas analyzer. The transducer module 22 and flowmeter 14 provide measurements to a processor (not shown) which determines cardiac output and pulmonary functions in accordance with Fick techniques implemented in software.

By applying a mathematical algorithm that combines and integrates concentration and volume over time, both the rate and amount of uptake (gain) or release (loss) of any constituent (indicator) can be determined in quasi-real time, that is, once every several breath cycles as opposed to real time which implies instantaneous, continuous reading. Cardiac output (the mean blood flow pumped by the heart) can thus be calculated using the well-established and accepted Fick Principle in real time using only breath-by-breath concentration information. It should be understood that a number of different non-invasive techniques for measuring cardiac output from respiratory gasses based on the Fick Principle have been proposed over the years. The system of the present invention can employ any one or combination of these Fick-based techniques, including modifications and improvements thereto, to determine cardiac output.

Because of the ability to measure the rate and amount of uptake as well as the end-tidal partial pressures of unique indicators such as nitrogen, nitrous oxide, anesthetic agents, and other inert gasses in real time, and/or concentrations of respired gasses such as oxygen and carbon dioxide, it has been possible to develop this unique noninvasive cardiac output monitor using the Fick Principle. While conventional gas analysis technology, such as IR spectroscopy, could be used to measure nitrous oxide and anesthetic agent concentrations, it is the unique ability to inexpensively measure nitrogen and other inert gasses such as helium that offers both a non-invasive but also a non-affecting, non-toxic approach. Furthermore, it is the ability to measure the density and viscosity properties of the inspired and respired gas mixture (e.g., with other technology one would have to measure the concentrations of all, not just some, constituents simultaneously) that allows for the measurement of the inspired and respired volumetric flowrate independent of the properties. By combining these gas analysis measurement techniques with accurate models and simulations of uptake and distribution of the gasses in the body, the current concept can be further refined to consider pulmonary shunts and deadspace as well as other individual-specific physiological and disease states.

In the invasive application of the Fick Principle technique classically referred to as the indicator dilution technique, a known amount of an easily detectable substance (indicator) is injected into the bloodstream and its presence is monitored a short, known, distance downstream. When the indicator and blood are completely mixed, the concentration-time relationship of the indicator provides information to determine the blood flow rate, which, by definition, is the cardiac output.

In accordance with one embodiment of the present invention, a non-invasive variation of the Fick technique is used and is suited to analysis of respiratory gasses with the gas analyzer of the present invention. Specifically, rather than directly (invasively) injecting an indicator into the bloodstream, a known volume/mass bolus of an indicator gas (e.g., nitrogen, nitrous oxide, sevoflurane, desflurane, or helium) is introduced into the inhaled respiratory gas stream of a patient breathing circuit. The blood will take up this gas via respiratory transfer in the alveoli of the lungs. In order to minimize the time it takes for the indicator to fill the alveolar space and to reduce the time required for the diffusion of the indicator into the bloodstream, the patient is ventilated at a predetermined, sufficient, breathing rate. The bolus of indicator gas is introduced during one or more quick inspired breaths. The blood will take up only a portion of the bolus of respiratory indicator gas, but that portion will behave in a manner similar to indicators injected directly into the bloodstream. The transfer of gas to the blood occurs because there is a difference in the partial pressure of the gas in the alveoli and in the blood stream. The alveolar partial pressure is higher than that in the blood, there being no (or a different amount of) gas in the blood. In the first inspired breath/breaths, the indicator enters the lungs. Subsequent inspired breaths will be free of indicator but will ensure uniform mixing in the lungs and will also start to dilute and evacuate the lungs. Within the first four or five exhaled breaths, the indicator gas that has not been taken up in the blood from the lungs will be completely (to over ninety-nine percent) removed.

The amount of indicator exhaled in these initial breaths is measured using the property detecting, multiple gas analyzer in conjunction with a respiratory flowmeter inline with the breathing circuit. The amount of indicator gas taken up by the blood is determined by subtracting the measured exhaled amount from the known input bolus. It is valid to perform this computation and measurement in the four or five breaths it takes to purge the lungs of the indicator gas, because there is no release of the indicator from the blood since the blood has not yet returned to the lungs after circulating through the body. The indicator gas is chosen to be one that has a low solubility in the tissues and so remains primarily in the blood. Nitrogen is such a gas. When the blood carrying the indicator gas returns to the lungs, there now exists a reverse difference in partial pressure between the blood and the alveoli. This time, the partial pressure in the blood is higher because there is no indicator in the alveoli. The end-tidal values (which approximate the arterial blood gas partial pressure) of indicator gas in each exhaled breath are measured and the amount and time history of the gas released from the bloodstream after it has circulated through the cardiovascular system is similarly measured. The total volume of exhaled indicator and the time it took to be released from the bloodstream, the area under the exhaled indicator gas-time curve, compared with the amount of indicator taken up, can be used to calculate the cardiac output using the Stewart-Hamilton relationship if no shunt or deadspace effects are present. The Stewart-Hamilton relationship is discussed and derived hereinbelow.

Indicator dilution techniques can be subdivided according to the method of application. Two commonly used techniques are continuous infusion and bolus injection. The continuous infusion method was first described by Stewart. A major disadvantage of this technique is that, in the closed circulatory system, the indicator eventually saturates the blood stream and any time history information is lost. The injection of a bolus of indicator, on the other hand, does not result in such saturation, and, although lower concentrations must be resolved, is used more often in clinical practice and is the technique that is a basis for a preferred embodiment of the present invention.

The principle of both methods can be illustrated by means of a simplified flow system in which a constant flow of fluid with a flow rate $Q_o$ and uniform velocity profile is assumed for a system with a single inlet, injection site, and outlet, detection site. Ideal, (i.e., complete) cross-sectional mixing is assumed throughout the volume of the system between injection and detection site.

For continuous infusion of indicator gas with injection rate $q_i$ into a steady blood flowrate $Q_o$, the volumetric concentration measured, $c_o$, after complete mixing has occurred, is constant and determined by the ratio of volumetric flowrate of indicator to flowrate of blood, $$c_o = q_i/Q_o \quad (3)$$

or, after rearranging and solving for the flowrate (e.g., cardiac output), $$Q_o = q_i/c_o. \quad (4)$$

When a bolus of indicator is injected into the blood stream, the relation between flowrate and concentration is obtained by using the condition of conservation of indicator. In an infinitesimally small time interval dt, the volume of indicator $dV_i$ passing out of the outlet equals the concentration of indicator at that time, $c_i(t)$, multiplied by the volume $dV_b$ of the blood passing by:

$$dV_i = c_i(t)\, dV_b \quad (5)$$

The blood volume $dV_b$ equals the blood flow rate, $Q_o(t)$, multiplied by the time interval dt, leading to $$dV_i = Q_o(t)\, c(t)\, dt \quad (6)$$

With use of the condition of conservation of mass, the total volume of indicator injected will pass the detection site, yielding:

$$V_i = \int_0^\infty Q_0(t) c_i(t) dt \quad (7)$$

For constant flow, the flow rate can be separated from the integral and solved for so that, $$Q_0 = \frac{V_i}{\int_0^\infty c_i(t) dt} \quad (8)$$

This equation is referred to as the Stewart-Hamilton equation. From this equation, the flow rate can be determined by the quotient of the total amount of indicator gas injected and the area under the measured indicator dilution curve. The $c_i(t)$ curve has an asymmetrical shape, which is caused by the continuation of the mixing process between indicator and transport medium, even when the first portion of indicator has already passed the detection site.

In the non-invasive dilution-indicator technique of the present invention, the indicator is a known gas constituent of a respiratory gas mixture. Preferred indicators are: nitrogen, nitrous oxide, helium and a relatively insoluble volatile anesthetic (sevoflurane, desflurane). At some initial time zero, a bolus of indicator gas is injected into the respiratory breathing gas and ventilated into the patient over a short time less than the inspiration period. Following injection, the ventilatory cycle is continued and the exhaled gas is analyzed and amount of the indicator gas exhaled during each breath is quantified. From the amount of gas measured in the exhaled volume, the content of indicator in the blood are calculated using Henry's Law. The measured concentration of indicator as a function of time elapsed is integrated over time to determine the total amount of indicator exhaled during the time interval. By incorporating this data (amount of indicator taken up by the blood and the area under the exhaled indicator time curve) into equation (8), the cardiac output is calculated. This technique is analogous to both dye and thermal dilution methods, but has the advantage of being low risk and noninvasive.

The assumptions used in the derivation of the Stewart-Hamilton equation for indicators include: (1) an open flow system (i.e., the indicator passes through only once); (2) no loss of indicator (i.e., no uptake in tissues); (3) complete cross-sectional mixing resulting in a uniform concentration distribution; and (4) constant flow (no transients). In clinical situations these conditions are rarely fulfilled when using direct injection of an indicator substance into the blood stream. Since the circulatory system is necessarily closed, recirculation of indicator will occur. Depending on the solubility of the indicator, loss of indicator cannot always be avoided. Depending on the injection and detection sites, adequate mixing may not always be achieved. And, most importantly, constant flow does not exist due to the pulsating cardiac action and effects of spontaneous or mechanical ventilation.

These factors are overcome in the present invention. By introducing into the blood stream a relatively small volume of indicator gas that is clear of indicator over a short period (i.e., less than the recirculation time), recirculation does not come into play. By using an insoluble gas, either nitrogen or very small amounts of relatively insoluble agents such as helium, nitrous oxide or sevoflurane or desflurane, the loss of indicator is extremely small or negligible and again any effects of recirculation are not significant. Since nitrogen is relatively insoluble compared to the other indicators, and the tissue compartments and venous blood are saturated, at equilibrium and constant, changes in arterial blood nitrogen content reflect directly the changes in the arterio-venous difference. By introducing the indicator into the respiratory gas during inhalation, mixing is not an issue, because the transfer through the microscopic capillaries in the alveoli ensures uniformity in the blood stream. Finally, by averaging at least three estimates over the ventilatory cycle, the effects of variable flow are minimized.

Although it is possible to accurately measure the variables described above, additional consideration is required to account for the presence of pulmonary shunts and deadspace in the lungs. Shunts are regions where blood vessels (capillaries) bypass the alveoli and as a result do not permit blood to come into contact with the indicator gas. Thus, in the presence of shunts, any cardiac output that is computed by the above-described procedure, while accurately computing the blood flow to the alveoli, could underestimate the actual blood flowrate because the shunt flow is not determined. Deadspace, on the other hand, is a region of the lungs where no transfer of indicator (or oxygen, etc.) takes place. This relates to what is known as lung capacity. Alveoli that do not contribute to blood gas transfer serve only to dilute the end-tidal value of the indicator. That is, when indicator is given up by the blood in working alveoli, gas with the indicator mixes with gas without the indicator from the deadspace. Therefore, in the presence of deadspace, any computation of cardiac output by the above-described procedure would overestimate blood flow because of lower end-tidal readings which suggest shorter residence time in the lungs of the blood and, hence, higher blood flow or cardiac output. The inability to compensate adequately for these two factors (i.e., shunts and deadspace) is a major shortcoming of indirect Fick techniques and probably the reason why such techniques have not been successful in the past.

In accordance with one embodiment of the present invention, in order to overcome this serious deficiency and at the same time provide a method for quantifying shunts and deadspace, the measured time-history of exhaled indicator is compared to results for the same time-history from a detailed physiological model of the human cardiovascular system that contains all the necessary parameters to describe the uptake, distribution and release of respired gasses. The Gas Uptake Distribution (GUS) model, developed by one of the present inventors, is a computer model that meets this requirement. The GUS model simulates respiratory and anesthetic gas uptake and distribution using a simplified, but functionally accurate, anatomical and physiological model of the human body. The simulation utilizes the patient parameters of weight and percent body fat, in conjunction with a parametric description of patient physiology (e.g., $O_2$ consumption, pulmonary shunt, systemic shunt, cardiac output, deadspace), ventilation mode (controlled, spontaneous, minute ventilation) and gas delivery (air, $O_2$, $N_2O$, anesthetics). Real time predictions of the concentrations, and uptakes or losses of any one of nine respiratory and anesthetic gasses in twelve compartments can be observed. The twelve compartments consist of eleven tissue compartments and one patient breathing circuit of either an anesthesia machine or mechanical ventilator. While the exemplary GUS model described herein involves twelve compartments, it will be understood that the GUS model can involve any number of suitable compartments sufficient to accurately model respiratory and anesthetic gas uptake and distribution in order to quantify the effects of deadspace and shunts.

The GUS model is integrated with the gas analyzer system microprocessor and is used to predict, in real time, the rate of exchange of an indicator between the alveolar gas and blood, the end tidal partial pressure of the indicator during normal and non-uniform ventilation. The simulation uses inputs based upon known patient data to make an initial prediction of alveolar partial pressure of the indicator. This initial approximation is then modified to predict the measured rates of uptake (gain) and release (loss) and end-tidal partial pressures of the indicator. Because the respiratory gas analyzer, in conjunction with a respiratory flowmeter (spirometer), can actually measure metabolic rates and $O_2$ consumption, and the ventilation parameters are known inputs, the only unknowns are the physiological parameters of shunts, deadspace and cardiac output. These are manipulated in real time using fuzzy logic as the simulation progresses to develop an output matching the measured parameters. The resulting values of shunts, deadspace and cardiac output represent an accurate estimate of the actual values. Once these values have converged at some value of cardiac output that incorporates shunts and deadspace, that value of cardiac output is reported as the output of the monitor.

The present invention offers significant advantages over other technologies that utilize the Fick Principle for determining cardiac output. As previously explained, the system of the present invention has the capability to determine cardiac output using any of the many recognized Fick techniques. By implementing the present invention, the clinician is not limited to a single application of the Fick Principle but is offered more flexibility by selection of appropriate techniques, methodologies, indicators, and algorithms for the calculation of cardiac output that fit the clinical situation. For example, currently available methods are limited to only one indicator (carbon dioxide or oxygen) at a time (e.g., the NICO system). With the present invention, any respiratory or anesthetic gas may be used as an indicator and more than one gas can be used simultaneously. This enables the clinician to select the appropriate indicator for the clinical situation.

The determination of the rate of uptake (gain) or release (loss) of a substance (indicator) in the alveolar gas is determined by multiplying the concentration of the substance (indicator) at the subject's airway by the airway flow and integrating the product over the respiratory cycle. Using this procedure the inspired and expired volume (mass) of the substance (indicator) is determined on a breath-by-breath basis. The gain/loss of the substance (indicator) can then be calculated as the difference between the inspired and expired substance volumes divided by the duration of each breath. This can be expressed as:

$$V_i(t)=(1/T_I)/V_i(t)c_i(t)dt-\{1/(T_E-T_I)\}/V_i(t)c_i(t)dt \text{ \{integrals\}} \quad (9)$$

where $V_i(t)$=airway flow volume per unit time $c_i(t)$=airway substance concentration $T_I$=end of inspiration (time)

$T_E$=end of expiration (time)

The fraction of the substance (indicator) at the patient's airway, $c_i(t)$, is multiplied by the airway flow, $V_i(t)$, and the product is integrated over the respiratory cycle. Using this procedure, the inspired and expired volume of the constituent (indicator) is determined on a breath-by-breath basis. The uptake (gain) or production (loss) can then be calculated as the difference between the inspired and expired volumes of the substance (indicator) divided by the duration of each breath. These values are then inserted directly into the Fick Equation for calculating cardiac output.

The Fick Principle described hereinabove was first articulated in 1870 by Adolf Fick and is easily derived from the basic laws of transport phenomena with the application of the Conservation of Mass to blood flowing through an organ system. The result of this derivation simply states that the flow of blood through an organ is equal to the total uptake or release of any substance (indicator) by the organ divided by the arteriovenous concentration difference of the substance (indicator). Another way of expressing the Fick principle is that the size of a stream may be readily calculated if we know the amount of substance (indicator) that enters or leaves the stream and the concentration difference resulting from such entry or removal. Both of these statements are true whether the substance (indicator) is a respiratory gas such as oxygen, carbon dioxide, nitrous oxide, or an intravenously injected substance such as cold normal saline.

The application of the Fick Principle to the measurement of pulmonary capillary blood flow enables the clinician to approximate cardiac output during steady-state conditions at normal levels of pulmonary shunting of blood. A mathematical application of the Conservation of Mass to a cardiopulmonary gas exchange model yields an expression for direct and indirect Fick techniques that has become known as the Fick Equation:

$$Q'=N'/(Ca-Cv) \quad (10)$$

where: Q'= pulmonary blood flow (cardiac output) (1 blood/min)

N'=rate of gain of substance (indicator) from alveolar gas (ml/min)

Ca=concentration of substance (indicator) in arterial blood (ml/l blood)

Cv=concentration of substance (indicator) in mixed venous blood (ml/l blood)

In order to apply the Fick Equation to determine pulmonary blood flow, techniques that can either directly measure or indirectly estimate the rate of exchange of a substance (indicator) between the blood and alveolus must be readily available. The same is true for determining the concentrations of the substance (indicator) in both the mixed venous and arterial blood. By incorporating this data into the Fick Equation, it is possible to calculate the pulmonary blood flow and thus cardiac output.

Numerous methods have been developed to determine each of the variables required for the calculation. These methods vary in computational complexity, equipment utilized, and the supervision required. Some methods involve invasive techniques (direct Fick) while others utilize various empirical correlations between noninvasive measurements and the variables of interest (indirect Fick). Various indicators including oxygen, carbon dioxide, nitrous oxide, and anesthetic gases have been used in these respiratory Fick techniques.

The use of direct (invasive) Fick techniques provides the most accurate prior known measurement of cardiac output. Unfortunately, direct techniques require sampling of both mixed venous and arterial blood in order to determine the amount of indicator in each. This requires the insertion of needles and catheters into the systemic circulation and heart in order to obtain the specimens required for analysis.

Indirect (noninvasive) Fick techniques rely on measurements of alveolar gas concentrations to estimate the amount of each indicator in arterial and mixed venous blood. Indirect (noninvasive) determinations of arterial substance (indicator) content have been made based on the partial pressure of the gas sampled at the patient's mouth at the end of a tidal expiration.

For the indirect Fick techniques, two assumptions are made. The first assumption is that the partial pressure of the gas sampled at the end of a tidal expiration (PiET) provides a good representation of the alveolar gas. Secondly, the alveolar gas is in equilibrium with the substance (indicator) in the arterial blood leaving the lungs. If these assumptions are valid, PiET can be used to estimate the arterial partial pressure of the substance (indicator). However, it is important to emphasize that by incorporating these assumptions, the accuracy of the calculation of cardiac output is limited during conditions a large pulmonary shunt and/or a large alveolar deadspace fraction. When these conditions exist, appropriate corrections to the estimation of cardiac output must be made.

To correct for the potential effects of a large pulmonary shunt and/or alveolar deadspace, a somewhat more detailed model of the cardiopulmonary system than the one used for the derivation of the Fick Equation is necessary. This model must allow for pulmonary shunting of blood flow and include an alveolar deadspace compartment. A pulmonary shunt represents pulmonary blood flow that perfuses regions of the lungs that are not being ventilated. An alveolar deadspace compartment is defined as a region of the lung that is being ventilated but is not being perfused. Application of the Fick principle for the indicator at the blood-lung interface results in:

$$Q'T-Q's=Q'T(1-\{Q's/Q'T\})=N/(Cv-Cal) \quad (11)$$

where Q'T=Total pulmonary blood flow (ml blood/min)

Q's=Blood flow that does not undergo gas exchange—shunt (ml blood/min)

N=Loss of indicator to alveolar gas (ml/min)

Cv=Concentration of indicator in mixed venous blood (ml/ml blood)

Cal=Concentration of indicator that has undergone gas exchange of indicator with alveolar gas (ml/ml blood)

Similarly, a mass balance of the indicator at the subject's airway, assuming that the alveolar deadspace empties in parallel, results in:

$$Cm*VT=CA(VT-VD)+CD*VD \quad (12)$$

where CA=concentration of indicator in alveolar gas (ml/ml gas)

Cm=Concentration of indicator measured at the subject's airway (ml/ml gas)

CD=Concentration of indicator measured in deadspace compartment (ml/ml gas)

VT=Tidal volume (ml)

VD=Alveolar deadspace (ml)

Solving for CA yields:

$$CA=(Cm*VT-CD*VD)/(VT-VD) \quad (13)$$

With the utilization of the various measurement techniques to determine the appropriate variables for these equations, cardiac output can be calculated with correction for any effects of shunt and deadspace incorporated into the final value.

The measurement of the variables used to calculate cardiac output is accomplished by utilizing three common Fick techniques: direct Fick, indirect Fick, and indicator-dilution. The variables to be measured are the uptake/release (gain/loss) and the arteriovenous concentration difference of the indicator. The present invention enables the clinician to measure these variables in numerous clinical situations. This approach offers significant advantages over other methods utilizing the Fick Principle for determining cardiac output.

As discussed above, in order to apply the Fick Equation to determine pulmonary blood flow (cardiac output), the rate of exchange of a substance (indicator) between the alveolar gas and blood and the arteriovenous difference of the substance (indicator) must be measured. Each of these variables is determined from the measurement of two other variables. The rate of exchange of the indicator can be determined by measuring the amount of indicator (constituent) that is present in both the inhaled and exhaled breath. The difference in amount between inspired and expired constituent is the net gain or loss of the indicator that is exchange between the alveolus and the blood. The arteriovenous difference of the indicator is determined by measuring/estimating the amount of indicator (constituent) that is present in both the arterial and mixed venous blood. The difference in these two values is the arteriovenous difference in the blood.

In accordance with the present invention, the determination of the rate of uptake (gain) or release (Goss) of a substance (indicator) in the alveolar gas is determined by multiplying the concentration of the substance (indicator) at the subject's airway by the airway flow and integrating the product over the respiratory cycle. Using this procedure the inspired and expired volume (mass) of the substance (indicator) is determined on a breath-by-breath basis. The gain/loss of the substance (indicator) can then be calculated as the difference between the inspired and expired substance volumes divided by the duration of each breath. This can be expressed as:

$$V(t)=1/TI \!/\!/ V'(t)F(t)dt - \{1/(TE-TI)\}\!/\!/V'(t)F(t)dt \text{ \{integrals\}} \quad (14)$$

where V'(t)=airway flow

F(t)=airway substance concentration

TI=end of inspiration (time)

TE=end of expiration (time)

A microcomputer is used to multiply the fraction of the substance (indicator) at the patient's airway, F(t), by the airway flow, V(t), and to integrate the product over the respiratory cycle. Using this procedure, the inspired and expired volume of the constituent (indicator) is determined on a breath-by-breath basis. The uptake (gain) or production (loss) can then be calculated as the difference between the inspired and expired volumes of the substance (indicator) divided by the duration of each breath. This value is then inserted directly into the Fick Equation for calculating cardiac output.

Because of the increased capability and versatility of the present invention, at least three unique techniques for measuring cardiac output noninvasively using the Fick Principle are possible. The first is an adaptation of the Soluble Inert Gas Technique. The second is an adaptation of the indicator-dilution method. The third is an integrated predictive computer model technique incorporating the computer simulation (e.g., the aforementioned Gas Uptake Simulation (GUS) model). As previously described, the GUS model can also be used to make correction for the presence of increased shunt and deadspace.

Several noninvasive respiratory applications of the Fick Principle are based upon the uptake and distribution of physiologically inert and soluble gases. When a soluble gas is inhaled, the partial pressure of the gas in the pulmonary capillary blood equilibrates with the partial pressure of the gas in the alveolar space. The volume of gas absorbed by the blood can be calculated directly from the partial pressure of the gas in the alveoli, the solubility of the gas in blood, and the quantity of blood that has equilibrated with gas. This can be expressed mathematically using Henry's Law as:

$$Vgas=Sgas*PAgas*Q \quad (15)$$

where:

Vgas=volume of gas absorbed by the pulmonary capillary blood (ml)

Sgas=solubility coefficient of the gas in blood (ml gas/ml blood/mm Hg)

PAgas=alveolar partial pressure of gas (mm Hg)

Q=volume of blood equilibrated with alveolar gas (ml blood)

Differentiating the expression with respect to time and rearranging terms result in $$Q'=V'gas/(Sgas*PAgas) \quad (16)$$

Equation (16) represents a special case of the Fick Equation where the mixed venous gas concentration is zero. The absence of the mixed venous term is due to the fact that under normal conditions the indicators used are not present in blood.

The use of a soluble inert gas as the indicator in the Fick Equation therefore eliminates the need to determine the mixed venous gas concentration provided that the mixed venous gas concentration is zero at the start of the measurement procedure. However, this zero concentration assumption requires that the measurement procedure be completed before the blood recirculation time.

Primarily two gases have been used as indicators in inert gas techniques, nitrous oxide and acetylene. For the present invention, nitrous oxide and the newer volatile anesthetic agents (sevoflurane, desflurane) are preferred over acetylene. These gases have a relatively low solubility in lung tissue and higher solubility in blood. Since high concentrations of these gasses in the blood are undesirable, low levels of inspired gas concentration must be used. This low level of inspired indicator concentration decreases the magnitude of both V'gas and PAgas in Equation (16), and therefore increases the sensitivity of the blood flow estimate to error in the determination of these parameters.

A number of techniques have been developed to increase the accuracy in measuring both V'gas and PAgas. These techniques have been discussed and include breath-holding techniques, rebreathing techniques and single-breath techniques.

One of the limitations of these techniques is the assumption that the venous concentration of the indicator gas is zero. This assumption not only limits the duration of the measurement of V'gas and PAgas due to venous recirculation, but also requires a waiting period between determinations to allow mixed venous blood content to decrease to zero. However, it is possible to overcome this limitation by using nitrogen as the indicator. Since nitrogen is relatively insoluble compared to the other indicators, and the tissue compartments and venous blood are saturated, at equilibrium and constant, changes in arterial blood nitrogen content would reflect directly the changes in the arteriovenous difference.

The above-described embodiment is a major improvement over existing non-invasive techniques in that it provides means for compensating for the effects of shunts and deadspace. However, the fuzzy logic used in estimating the effects of shunts and deadspace may not resolve certain ambiguities that may arise. Another, more general embodiment of the present invention involves separately estimating the deadspace (both physiological and anatomical) so that only shunts need to be iterated in the physiological model software. In addition, in some cases, it may be inconvenient to provide indicator gasses that need to be tracked; accordingly, the second embodiment utilizes the unique instantaneous relationships between oxygen and carbon dioxide to provide much the same information.

In "Deadspace and the Single Breath Test for Carbon Dioxide During Anesthesia and Artificial Ventilation," Br. J. Anaesth (1984), 56, 109, incorporated herein by reference in its entirety, Fletcher et al. teach that the anatomical deadspace (i.e., the deadspace of the passages in the lungs that bring the ventilatory gasses to the alveoli) can be accurately measured by measuring the total volume of expired gasses before any change occurs from that inspired in measured concentration of either oxygen and carbon dioxide. Further, Fletcher teaches that the physiological deadspace (i.e., the measure of the alveoli that do not participate in transfer of gasses to the blood) can be estimated quite accurately by measuring the volume of expired gasses during alveolar release. Using relatively simple algorithms, this deadspace is related to the slope of the concentration-volume trace as end-tidal values are approached.

Kim et al. teach in the aforementioned paper that the value of the mixed venous carbon dioxide partial pressure is related to the value of the exhaled carbon dioxide concentration at the point when the ratio of the change of carbon dioxide concentration to the change in oxygen concentration (i.e., the instantaneous respiratory quotient) is approximately 0.3. This ratio value is a function of physiological conditions as well as disease state; however, by applying the method of Fletcher et al. to account for deadspace, the variation may be limited to shunts alone. Since cardiac output (not including the effects of shunts) is thus defined by the Fick equation to be the ratio of the carbon dioxide produced to the difference in mixed venous and arterial carbon dioxide partial pressures, this portion of the calculated cardiac output may be introduced into the physiological model software (e.g., GUS) and a shunt value iterated that results in the respired breath waveform as measured. In cases where it is reasonable to assume that shunts do not play a major part (e.g., when they are not present or remain constant during the period of monitoring), the data from the gas analyzer and respiratory flow meter provide cardiac output directly, with accuracy that is superior to existing modified-Fick techniques. A detailed example of a modified Kim single-breath technique is now provided.

Given that the system of the present invention can inexpensively and reliably measure real time, simultaneous $O_2$ and $CO_2$ concentrations (and $N_2$ if needed) as well as consumption and production right at the patient breathing circuit, single-breath techniques can reliably be use to non-invasively measure cardiac output and provide continuous determination of cardiac output on a breath-by-breath basis.

As described in the aforementioned paper, Kim et al. developed a method of estimating "true" mixed-venous and arterial $CO_2$ partial pressures by the analysis of simultaneous exhaled $O_2$ and $CO_2$ partial pressures (Feo$_2$ and Feco$_2$) on the alveolar plateau of a single extended exhaled breath. Given either $O_2$ consumption or $CO_2$ production cardiac output can then be estimated using the Fick equation. Several studies have been undertaken since then that have attempted to validate and improve the technique, mostly from a data processing perspective. However, this methodology heretofore has not received wide acceptance primarily for three reasons. The first reason is the difficulty associated with obtaining simultaneous realtime $O_2$ and $CO_2$ data, putting the technique into a very high cost category. This limitation has been overcome in the present invention with the use of the aforementioned real time multi-gas analyzer. The second reason is the extensive calculations that must be performed. This limitation has been overcome in the present invention by using state-of-the-art microprocessor technology. The third reason is the concern about the validity of the assumptions that were made in the original methodology. These concerns focus upon the potential effect of any body gas stores, alveolar deadspace and pulmonary shunts vis à vis disease state, the shape of the oxyhemoglobin and carbon dioxide dissociation curves, the necessity for a relative steady state (also required theoretically for any Fick and single-injection indicator-dilution methods), and the existence of any ventilation/perfusion (V'/Q) abnormalities (the effect of sequential emptying of the alveoli). Most of the assumptions made by the original investigators have subsequently been validated, but concerns have been expressed over using the technique in patients with abnormal ventilation/perfusion ratios (V'/Q). These concerns have generally been overcome by the significant number of studies that have categorically confirmed that there is sufficient information in the respired $CO_2$ data alone that correlates with cardiac output. The former have been studies based on the initial efforts of Fletcher who identified a very accurate technique to account for deadspace, and have culminated with the very recent work of Arnold et al. who conducted detailed correlations of exhaled $CO_2$ waveforms at various work/exercise levels to cardiac output. These latter studies clearly confirm that the $CO_2$ waveform has strong predictive elements relating to cardiac output.

In view of these studies, the present inventors have determined that if the true instantaneous alveolar values of $O_2$ and $CO_2$ that account for lung volume and physiological deadspace can be computed/measured, the true instantaneous respiratory exchange ratio can be determined directly for the alveoli, thereby allowing computation of the actual blood flow being passed through the lungs. Pulmonary and systemic shunting is accounted for with knowledge of the arterial oxygen saturation, which is routinely measured in a peripheral artery with a pulse oximeter. According to the methodology of the present invention, the single-breath technique is augmented to account for V'/Q abnormalities. This is accomplish by modeling the physiology and, therefore, having a viru patient on the side to compare with. The inputs of deadspace and cardiac output to the physiological model are iterated until the model converges on the measured metabolic outputs.

Figure 5:
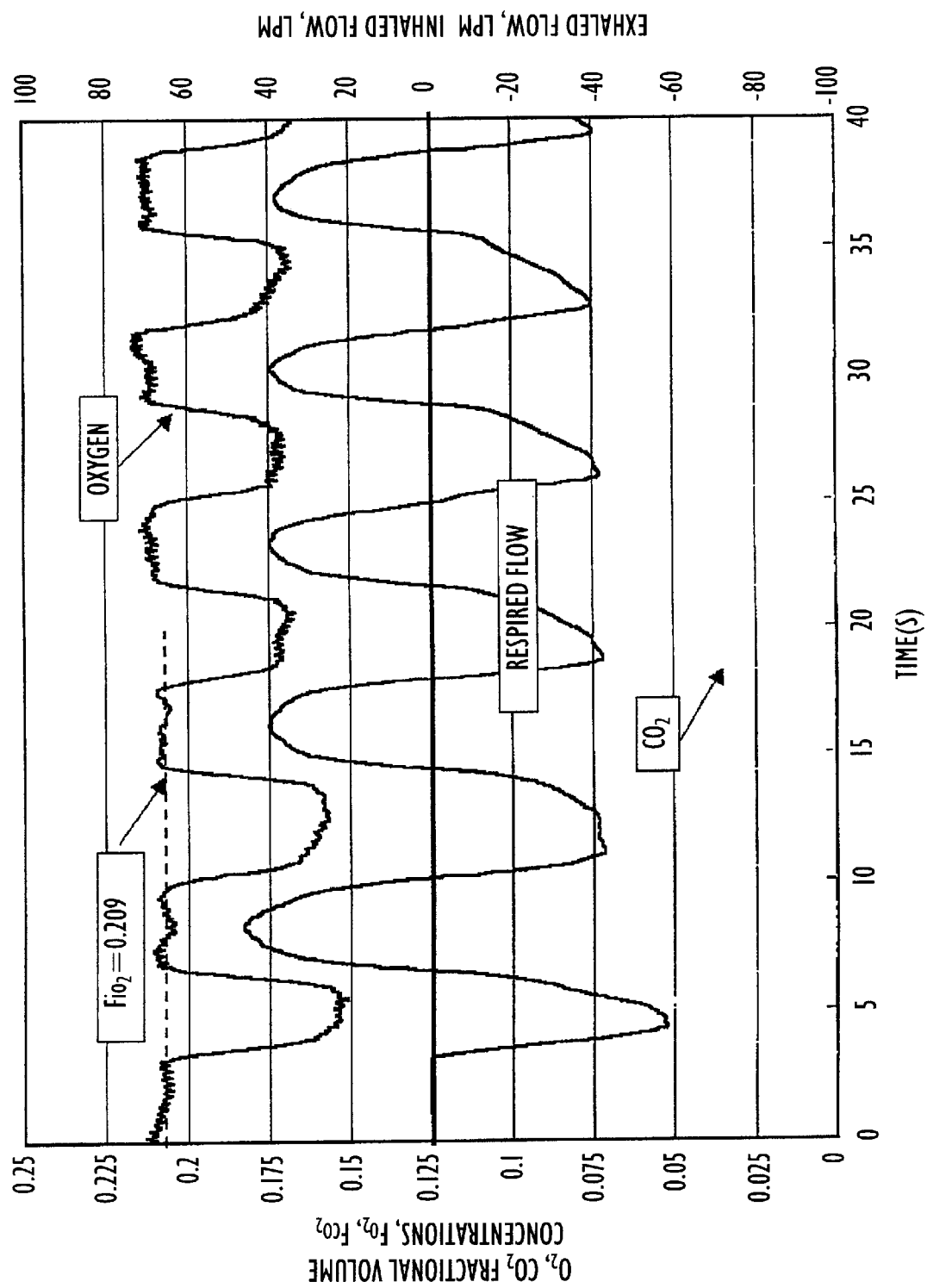
FIG. 5 is a graph showing typical measured respiration parameters, including instantaneous respired flow rate and $O_2$ and $CO_2$ concentrations.
Figure 6:
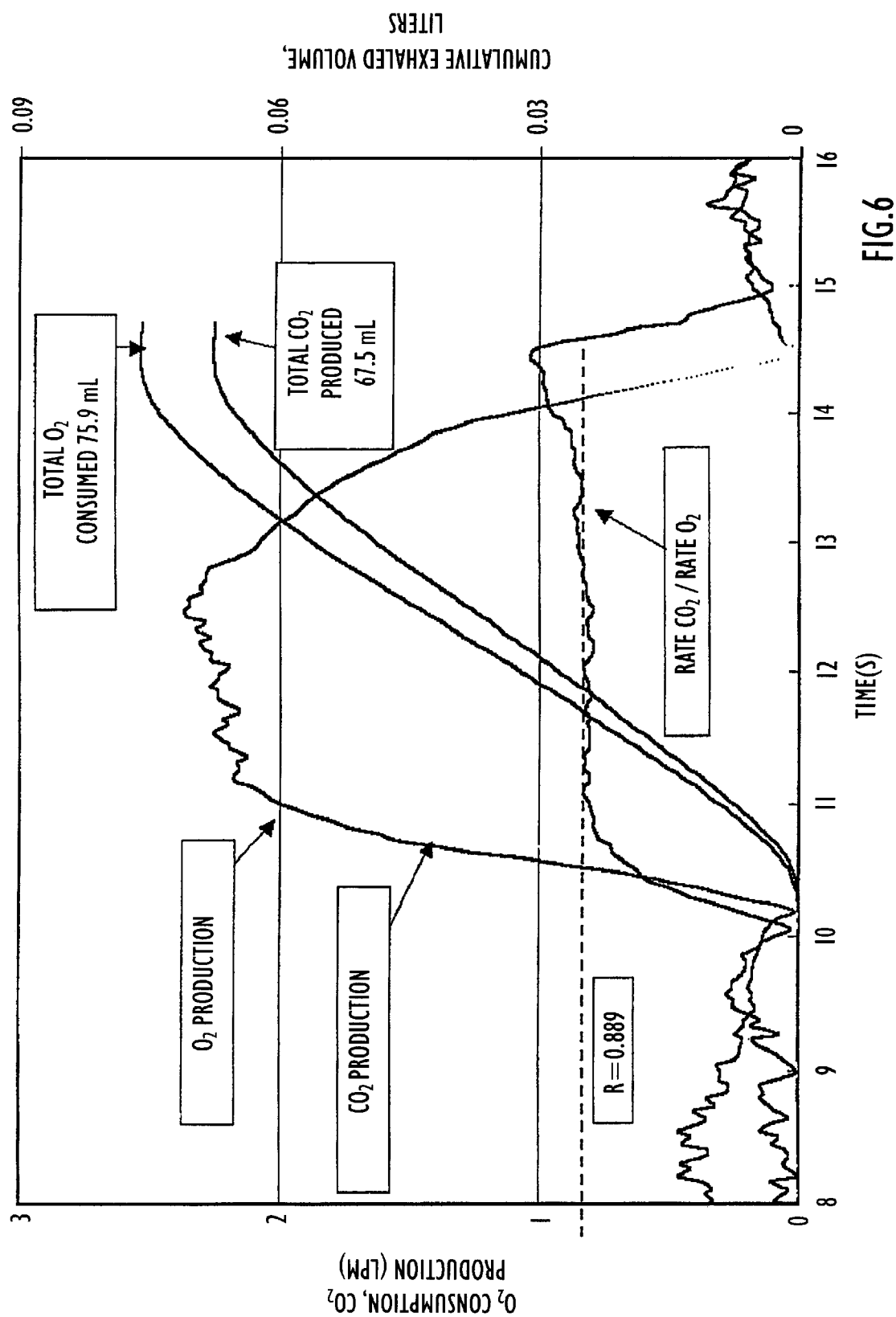
FIG. 6 is a graph illustrating the rates of $O_2$ consumption and $CO_2$ production, their ratio, and total volumes consumed and produced for a single breath.
Figure 7:
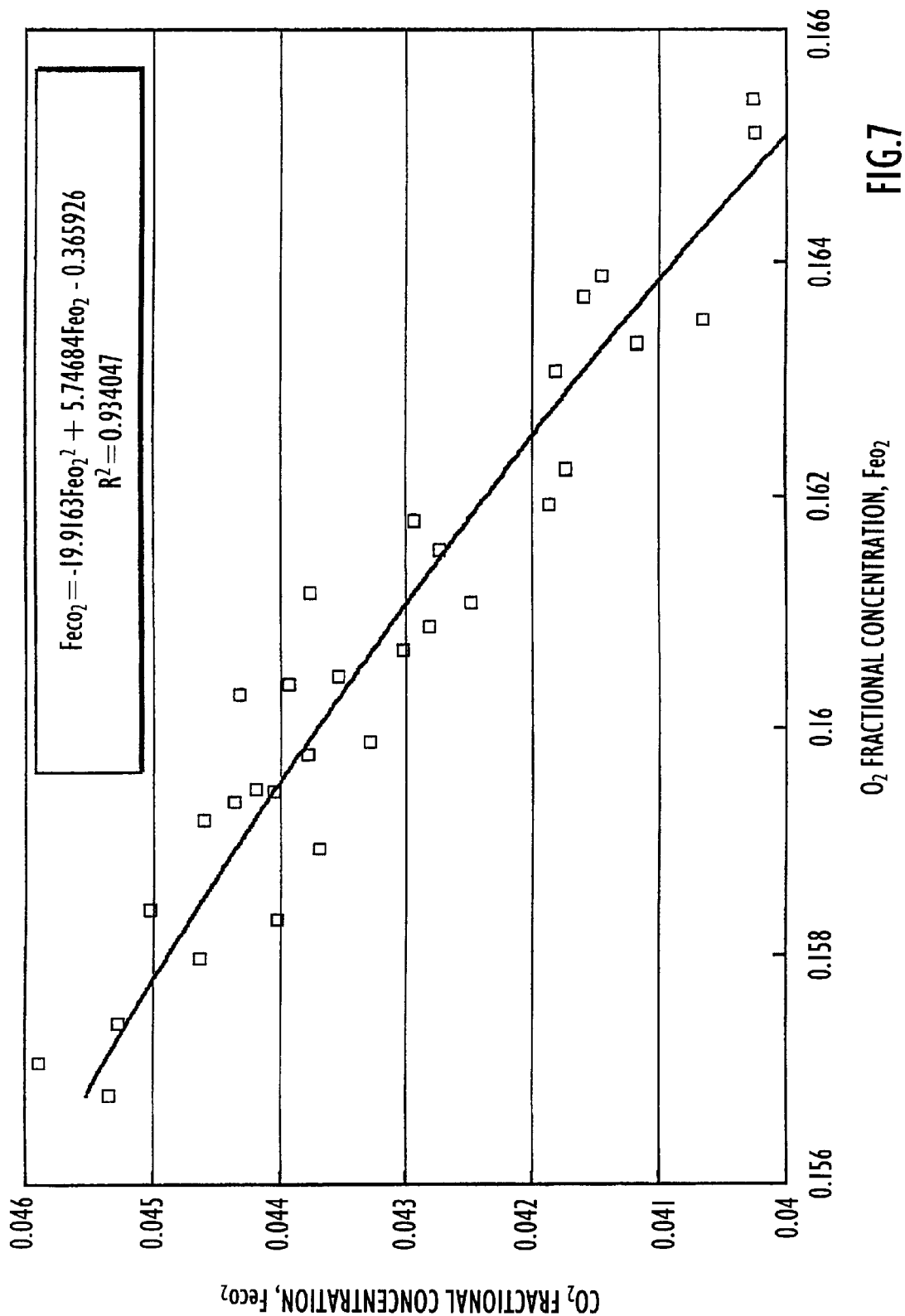
FIG. 7 is a graph showing the single breath $CO_2$ versus $O_2$ concentrations for the alveolar plateau region.
Figure 8:
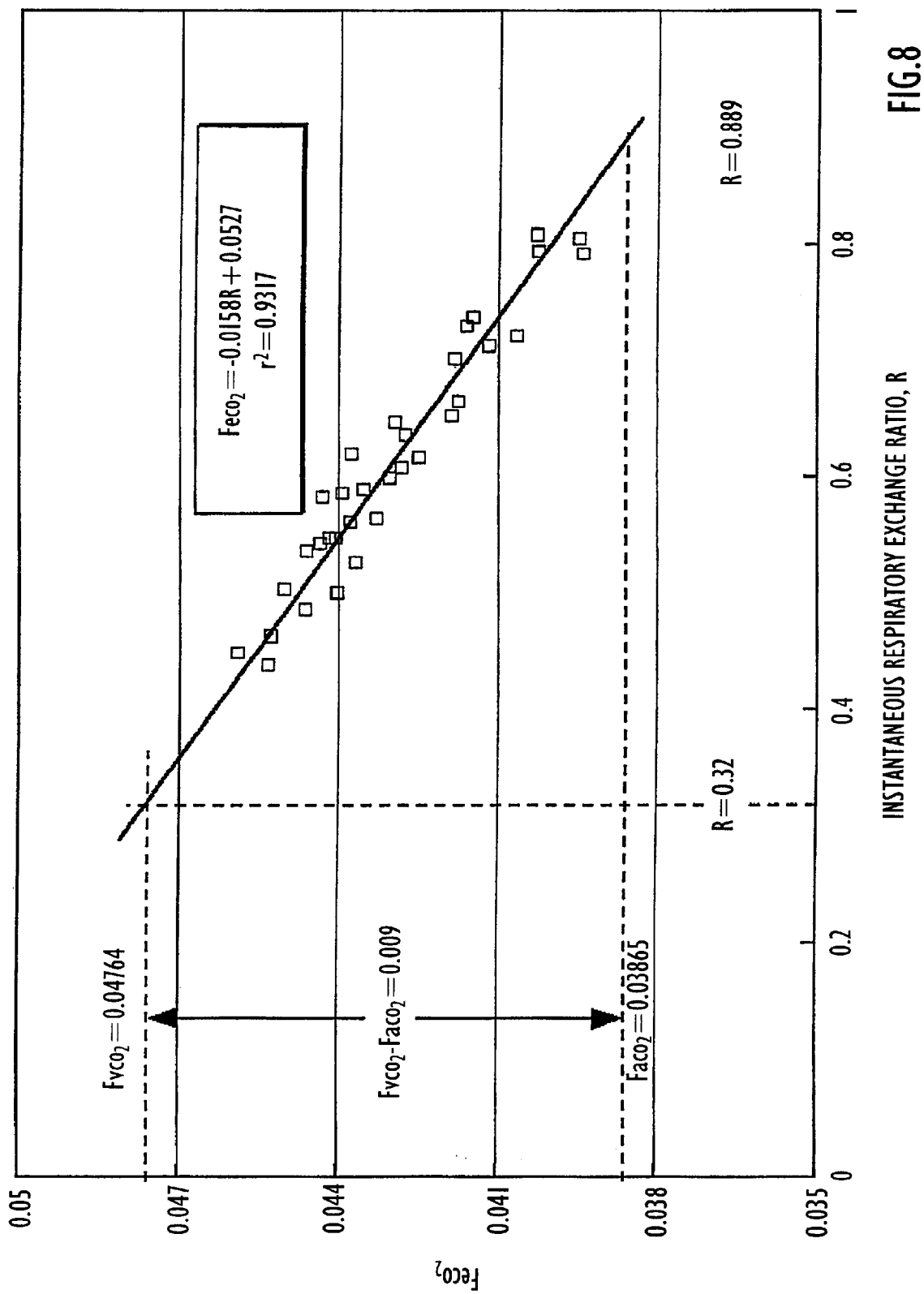
FIG. 8 is a graph illustrating a typical alveolar $CO_2$ concentration versus instantaneous respiratory exchange ratio.
Figure 9:
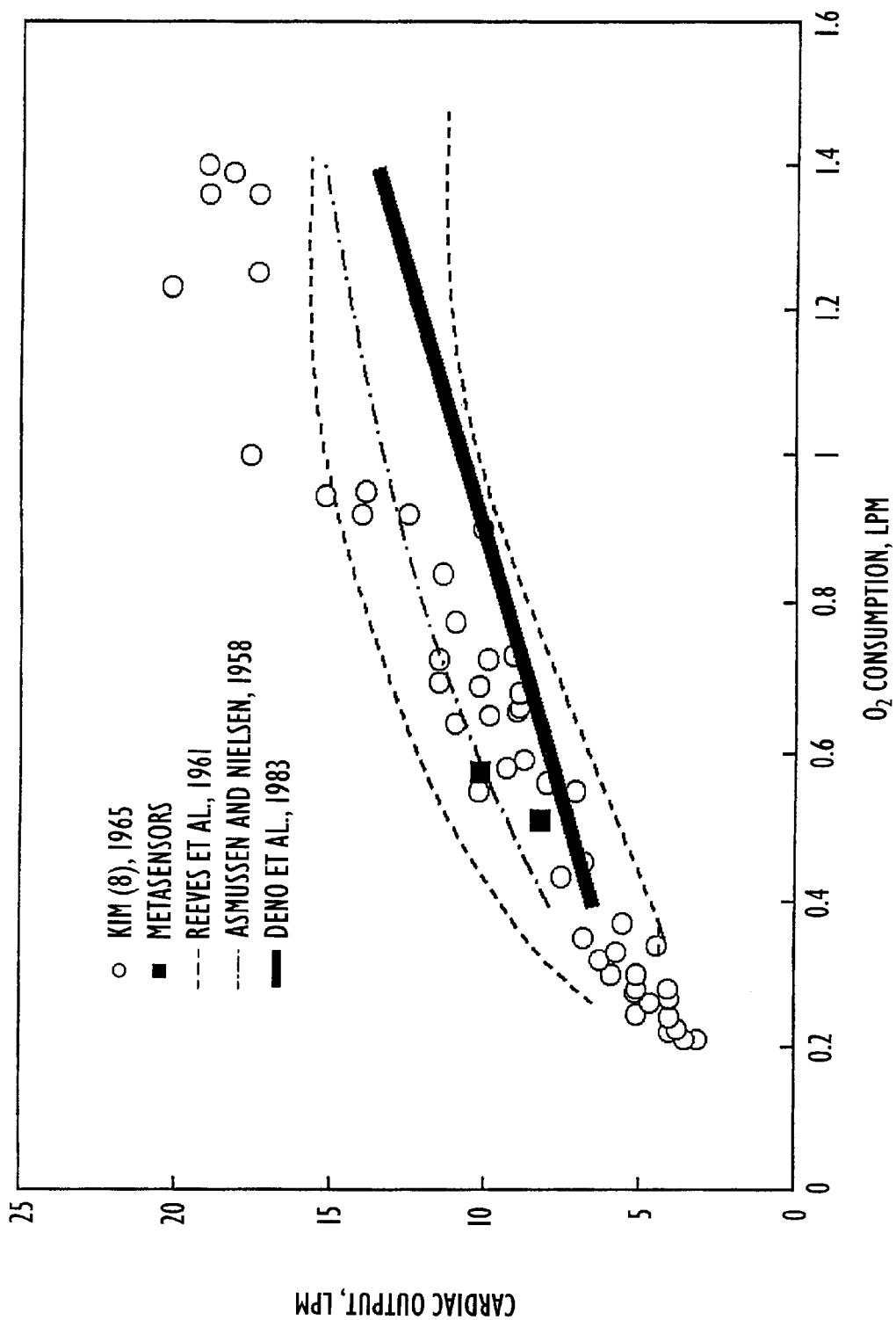
FIG. 9 is a graph showing cardiac output versus $O_2$ consumption resulting from a variety of research studies.

Using the cardiac output monitor 10 shown in FIG. 4, experimental data was collected and the computations required to determine cardiac output were performed, as shown in FIGS. 5–8. FIG. 5 shows the typically measured respiration parameters, inspired and exhaled $O_2$ and $CO_2$ concentrations and instantaneous respired flowrate, for several breaths. From this data all other parameters are computed. FIG. 6 illustrates the rates of $O_2$ and $CO_2$ consumption and production, their ratio (respiratory quotient), and total volumes consumed and produced for the second breath. FIG. 7 shows the single breath $Fco_2$ plotted against $Fo_2$ for the alveolar plateau region. This data is processed to obtain a relationship between alveolar $CO_2$ concentration and instantaneous exchange ratio, R, (accounting for deadspace) shown in FIG. 8. Note that the data spans the range of exchange ratio between approximately 0.2 and 0.8 so that only a minor extrapolation to the steady state respiratory exchange ratio ($R_{SS}$) is required. $R_{SS}$ is calculated by integrating the product of the concentration and the flowrate. For this case, $R_{SS}$=0.889; however, it should be noted that it also equals the ratio of the $CO_2$ production to $O_2$ consumption rates shown in FIG. 6. Using the mixed venous and arterial values estimated from the points when R=0.32 and R=0.889, an arterio-venous difference of 0.9% (6.84 mmHg) is obtained. The minute oxygen consumption from FIG. 6 is 75.9 ml in the breath of 7.925 s or 575 ml/min. This results in a cardiac output for that particular breath of approximately 10.17 liters/min, which is consistent with the active state of the subject, and falls within expected ranges as shown in the data of numerous other researchers in FIG. 9.

The diagnostic capability of this methodology is considerably greater than merely providing cardiac output. Metabolic rate has been computed and can be reported to the user/clinician. Deadspace and pulmonary shunts can be quantified; information that would be of significant interest to the respiratory therapist as well as the pulmonologist.

In Kim's technique, the lungs act as an aerotonometer that measures the partial pressure of the mixed venous blood, and hence gas content. The essential feature of Kim's method is the application of the Haldane principle to determine the mixed venous and arterial $CO_2$ partial pressures ($Pvco_2$ and $P_Aco_2$) from simultaneous measurements of $CO_2$ and $O_2$ concentrations from a single exhalation that is long enough to ensure that alveolar gasses have equilibrated and that enough data points can be collected on the alveolar plateau (where the exhaled gasses are representative of the alveolar gasses) for a statistically meaningful regression analysis to be performed. Henry's Law of Solubility and the dissociation curves relate alveolar partial pressures and the content in the blood for $CO_2$ and $O_2$. Using the cardiac output monitor of the present invention, with sample rates of 30–200 per second, data taken under normal respiratory rates of 8–12 breaths per minute yield satisfactory results; thus, patient cooperation is not required. Assuming that mixed-venous $CO_2$ tension $Pvco_2$ remains constant during this time (blood normally does not recirculate in the period of one breath), then arterial $CO_2$ tension ($Paco_2$) will rise and eventually, if the breath is long enough, will approach $Pvco_2$. Haldane observed that the arterial value is equal to the mixed venous value when the instantaneous respiratory exchange ratio, $R=V'_{CO2}/V'_{O2}=0.32$. A detailed discussion of data supporting this observation is presented by Kim et al. and will not be repeated here.

Kim, however, made the assumption that the exhaled concentrations were equal to the alveolar values. Clearly, this would hold true only if there were no alveolar deadspace. The relationship of $Pco_2$ with R should, of course, be correct for the air exhaled from a fully ventilated and perfused alveolus. This means that the exhaled $O_2$ and $CO_2$ tensions must be corrected to true or "ideal" alveolar values in order to account for the dilutionary effects of the unmetabolized gasses in the deadspace. The "ideal" alveolar partial pressure is a term used herein to indicate that any effects of physiologic deadspace have been incorporated. Physiologic deadspace is defined as a region of the lung that is being ventilated but is not being perfused. The Bohr equation allows correction of the exhaled tensions (of gas X, that is, $CO_2$ and $O_2$) for physiologic deadspace, if deadspace and expiratory volume, $V_E$, can be quantified.

$$V_{PHYSD}/V_E = [P_{AX} - P_{EX}]/[P_{AX} - P_{IX}] \tag{17}$$

In accordance with the present invention, the physiologic dead space volume, $V_{PHYSD}$, is quantified using Fletcher's analysis of the single breath $CO_2$ concentration (i.e., the expired volume waveform), which is collected by the cardiac output monitor (see FIG. 5). The exhaled gas tidal volume, $V_E$, is determined by integrating the expired flowrate using the property-compensated pneumotachometer. The gas analyzer of the present invention measures the partial pressures in the exhaled gas, $P_{EX}$, and the inhaled gas, $P_{IX}$. This then leaves the "ideal" alveolar partial pressure, $P_{AX}$, as an unknown.

Fletcher considered physiological deadspace ($V_{PHYSD}$) in terms of two components: convective airway and alveolar deadspace. Convective airway deadspace ($V_{DAW}$) extends from the lips to the interface between the inspired and alveolar gas. Alveolar deadspace ($V_{DALV}$) includes deadspace caused by ventilation-perfusion ratio mismatching within terminal respiratory units; ventilation-perfusion ratio mismatching between units; venous admixture or right to left shunt; and temporal deadspace. Classical methods for estimating $V_{PHYSD}$ are based on collection of expired air over a period of a few minutes during steady state with simultaneous sampling of arterial blood. The partial pressure of $CO_2$ is measured from both samples and $V_{PHYSD}$ is calculated by using Bohr's equation. Fletcher determines this deadspace with a single breath test of $CO_2$ (SBT-$CO_2$).

Figure 10:
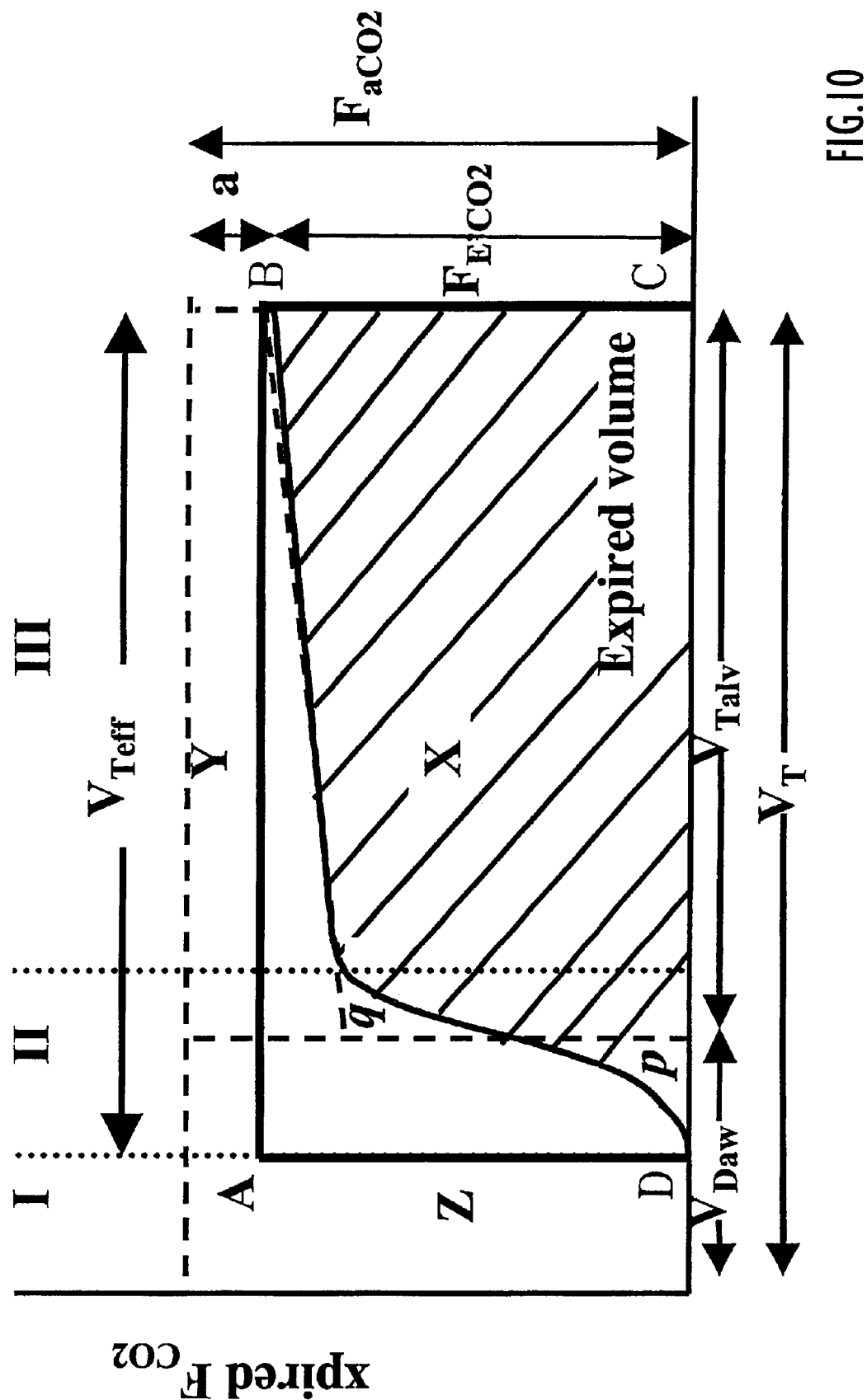
FIG. 10 is a graph showing expired $CO_2$ fraction versus expired volume that is useful for determining deadspace.
Figure 11:
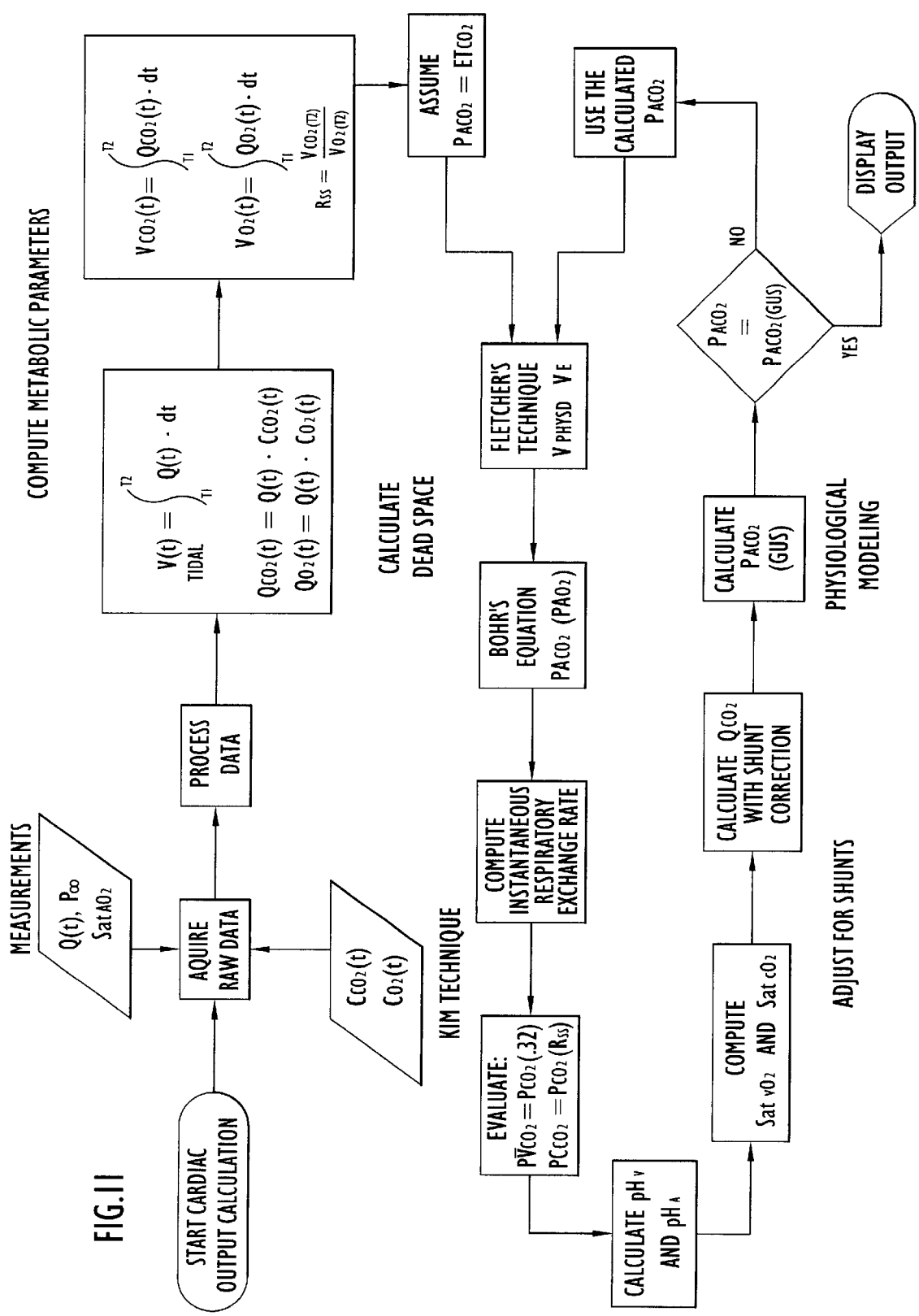
FIG. 11 is a flowchart illustrating an iterative technique for determining cardiac output, shunts and deadspace in accordance with an exemplary embodiment of the present invention.

In accordance with Fletcher's technique, a plot of expired $CO_2$ fraction ($F_{ECO2}$) against expired volume based on the SBT-$CO_2$ is generated, as shown in FIG. 10. Phase I defines conducting airway deadspace. Phase II defines the transition between conducting airway and alveolar gas. Phase III defines the alveolar plateau, representing $CO_2$ rich gas from the alveoli. Phase II and m together represent the effective tidal volume ($V_{Teff}$) that contributes to gas exchange. Fletcher then divides the single breath into regions X, Y, and Z (FIG. 10). Area X represents tidal elimination of carbon dioxide ($V_{TCO2}$) with effective part of $V_T$. Area Y represents wasted ventilation as a result of $V_{DALV}$.

Area Z represents wasted ventilation as a result of $V_{DAW}$. The areas are used to express the deadspace fractions: $V_{DAW}/V_T=Z/(X+Y+Z)$; $V_{DALV}/V_T=Y/(X\ 30\ Y+Z)$; $V_{DAW}/V_{TALV}=Y/(X+Y)$, and $V_{PHYSD}/V_T=Y+Z/(X+Y+Z)$. The dashed line at the top of the graph represents the fraction of the $CO_2$ of a gas in equilibrium with arterial blood ($Fa_{CO2}$). The partial pressure of $CO_2$ in the exhaled breath is not equal to the partial pressure of $CO_2$ in the alveoli, because of admixture of gas from ventilation-perfusion ratio mismatched alveoli and gas from alveoli with efficient gas exchange. If $Fa_{CO2}$ is not known, the value can be estimated by extrapolating the curve out to an exhaled volume equivalent to 15% of the predicted Total Lung Capacity. Extrapolation is effective for normal individuals and patients with airway disease, but not patients with pulmonary embolism.

During mechanical ventilation, gas compression increases $V_{DALV}$ and equipment dead-space alters $V_{DAW}$, and Phase II may be difficult to distinguish from Phase III. To extract information from readily obtained data, the present inventors propose a method closely related to Bohr's concept in which end-tidal carbon dioxide ($F_{ETCO2}$) is related to the exhaled carbon dioxide ($F_{ECO2}$). $V_{TCO2}$ (area X) is related to the volume of $CO_2$ hypothetically eliminated by a breath in which the whole effective volume has $CO_2$ fraction $F_{ECO2}$ equal to area ABCDA. The ratio, X/areaABCDA=$V_{TCO2}$/[$V_{TEFF}$ $F_{ECO2}$] describes the efficiency of the effective volume in eliminating $CO_2$.

Fundamentally, one needs to know alveolar concentrations in order to calculate deadspace, but one needs to know deadspace to calculate alveolar concentrations. To resolve this dilemma, the present inventors propose to develop a "vital patient" consisting of a physiological model of respiratory gas uptake and distribution which will be used to mimic the real patient, matching the patient's actual measured gas exchange values. One such model is aforementioned GUS model, which simulates respiratory gas uptake and distribution using a simplified anatomical and physiological model. The simulation uses patient parameters (e.g., weight, percent body fat), patient physiology (e.g., $O_2$ consumption, pulmonary shunt, systemic shunt, cardiac output, deadspace), ventilation mode (e.g., controlled, spontaneous, minute ventilation), and gas delivery (e.g., air, $O_2$, $N_2O$, anesthetics). Predictions of the concentrations and uptakes or losses of the respiratory or indicator gasses in twelve (or any appropriate number) compartments can be observed. Again, the compartments include eleven tissue compartments and one patient breathing circuit of either an anesthesia machine or mechanical ventilator.

The GUS model is integrated into the computational scheme and is used to predict real time rate of exchange of $O_2$ and $CO_2$ between the alveolar gas and blood, as well as the exhaled partial pressures during normal and nonuniform ventilation, and iterated until what the model output corresponds to what the patient is producing. A specific example of the iterative process is outlined in the flowchart shown in FIG. 11 and described below.

First, an initial guess is made for physiologic deadspace by calculating the value by Fletcher's technique using the measured $CO_2$-volume waveform and the measured end-tidal $CO_2$ tension as an initial guess for the alveolar value. From this estimate and Bohr's equation, alveolar $O_2$ is obtained and the procedure outlined below for computing cardiac output is performed. The resultant value of cardiac output is provided as an input to the GUS model, and a prediction of alveolar and exhaled partial pressures of $O_2$ and $CO_2$ is made. If the partial pressures agree with the measured values then the cardiac output is accepted. If the values differ, the alveolar $CO_2$ values computed by GUS are used as the next input and the iteration continues. When the simulation has converged to within a predetermined difference with the measured values, cardiac output is accepted and represents the value that has been corrected for shunt and deadspace.

Given the measurements of instantaneous [$P_{Ii}(t)$, $P_{Ei}(t)$] and end-tidal partial pressures [$P_{ETi}$] of $O_2$ and $CO_2$ and the "ideal" alveolar partial pressures (from Bohr's equation using the first estimate of deadspace from the GUS model) for each incremental volume as a function of time during the exhaled breath, an equation for the instantaneous respiratory exchange ratio (R) is derived from a mass balance of inhaled and exhaled $N_2$ (which is not taken up), from which, both the mixed-venous and arterial values of $CO_2$ concentration are computed. From the definition of the instantaneous respiratory exchange ratio, R, ($R_{SS}$ is the steady state respiratory quotient), $$R=[C_{ACO2}(t)V'_{Ao}(t)-C_{ICO2}\,V'_{AI}(t)]/[C_{IO2}(t)V'_{AI}(t)-C_{AO2}(t)V'_{Ao}(t)]. \quad (18)$$

After some considerable manipulation, a relationship between the alveolar concentrations of $CO_2$ and $O_2$, the general alveolar air equation, which includes the effects of all deadspace is derived, $$P_{ACO2}(t)=(P_\infty-P_{47})[R\,F_{IO2}+F_{ICO2}]/[1-(1-R)\,F_{IO2}]-P_{AO2}(t)[R+(1-R)F_{ICO2}]/[1-(1-R)F_{IO2}]. \quad (19)$$

Measured values of $P_{ACO2}$, and $P_{AO2}$ are used to determine R and the $P_{ACO2}$ at R=0.32 defines the true mixed venous value. The value at R=$R_{SS}$ defines the true arterial value. Note that the arterial value of $CO_2$ does not necessarily coincide with the end-tidal value: a cause for inaccuracy when using indirect Fick techniques.

The $O_2$ consumption and $CO_2$ production (V'$O_2$ and V'$co_2$) for the breath is measured. Pulmonary capillary blood flow, $Q_{PCBF}$, is then determined by the indirect Fick technique with the assumptions: 1) instantaneous R reflects gas exchange between pulmonary capillary blood and alveolar gas and 2) the $CO_2$ dissociation curve is linear, or at least parallel. Using a value of, for example, 4.7 ml/liter per mmHg $Pa_{CO2}$ for the slope of the whole-body $CO_2$ dissociation curve at rest, the pulmonary capillary blood flow, $Q_{PCBF}$, is:

$$Q_{PCBF}=V'_{O2}(R_{SS}=0.32)/[4.7(Pv_{O2}-Pa_{CO2})]. \quad (20)$$

The slope of the $CO_2$ dissociation curve can be refined if arterial $O_2$ saturation and hemoglobin are known or can be adjusted for the metabolic conditions given the approximate level of $CO_2$.

The pulmonary capillary blood flow approximates the systemic cardiac output when no significant pulmonary shunt is present. A pulmonary shunt is blood flow that perfuses unventilated regions of the lungs. A pulmonary shunt dilutes pulmonary capillary blood flow. Using conservation of mass, the systemic cardiac output, $Q_{CO}$, can be expressed as:

$$Q_{CO}=Q_{PCBF}+Q_S \quad (21)$$

where $Q_S$ is the pulmonary shunt blood flow. The mass balance for $O_2$ in the blood is, $$C_aQ_{CO}=C_VQ_S+C_CQ_{PCBF} \quad (22)$$

where $C_a$ is the systemic arterial $O_2$ content, $C_V$ is the mixed venous $O_2$ content, and $C_C$ is the pulmonary capillary $O_2$ content. From these relationships an equation for determining the flow through the pulmonary shunt can be derived, where $O_2$ content can be expressed as $\alpha\,P_{O2}+1.39\,Hb_4\,Sat_{O2}$, $\alpha$ is solubility of $O_2$ in blood, $Hb_4$ is hemoglobin level, Sat is $O_2$ blood saturation, and, $P_{O2}$ is partial pressures of $O_2$ in arterial, capillary or venous blood. The arterial $O_2$ saturation (Sata$_{O2}$) is measured directly using a pulse oximeter. Since the amount of the dissolved $O_2$ in the arterial, venous and capillary blood ($\alpha P_{O2}$) is relatively small compared to the amount combined with hemoglobin, it is ignored. The equation for cardiac output thus becomes, $$Q_{CO}=Q_{PCBF}[Satc_{O2}-Satv_{O2}]/[Sata_{O2}-Satv_{O2}]. \quad (23)$$

In order to solve the equation, capillary and mixed venous $O_2$ saturation are obtained from the $O_2$ dissociation curve for hemoglobin. The Margaria equation provides a convenient form:

$$Sat_{O2}=[\{m-1\}K^4P_{O2}^4+KP_{O2}\{KP_{O2}+1\}^3]/[\{m-1\}K^4P_{O2}^4+\{KP_{O2}+1\}^4] \quad (24)$$

where, $Sat_{O2}$=fractional oxygen saturation, $P_{O2}$=$O_2$ partial pressure, m=empirical constant=124, K=empirical constant dependent on pH and temperature. DeFilippe's data shows that the adjustable constant, K, for $6.8 \leq pH \leq 7.8$ and $293° K. \leq T \leq 318° K.$, is, $$K=[0.796\{pH-7.0\}/7.0+0.152\{pH-7.0\}/7.0+0.0211]\exp[-17.72\{T-293\}/T]. \quad (25)$$

The pH effect is especially important because pH varies along the length of the capillary due to $CO_2$ transport. For normal blood (protein content≈7%), the relationship of pH to $P_{CO2}$ is:

$$pH=-0.3782 \ln P_{CO2}+8.806 \quad (26)$$

so that the pH may be calculated from the values of $P_{CO2}$ obtained from the analysis of pulmonary capillary blood flow. Once the various $O_2$ contents have been calculated, $Q_{CO}$ may be calculated since $Q_{PCBF}$ has already been determined. $Q_{CO}$ is the value reported to GUS if the solutions do not match and to the clinician when convergence has been achieved.

While the cardiac output monitoring system of the present invention has been described in conjunction with the use of specific Fick techniques and methodologies, it will be understood that the system of the present invention can be used with any technique that is based on the Fick principle and that determines cardiac output from alveolar gas concentrations, including, but not limited to any. oxygen-based Fick techniques, carbon dioxide-based Fick technique, differential carbon dioxide Fick techniques, Fick techniques involving computer modeling using respiratory gasses, and soluble insert gas Fick techniques. An overview of such techniques is provided by Capek in "Fick Techniques," Enc. of Med. Devices and Instr., Wester, J. D. (editor), Wiley, N.Y., pp. 1302–1314 (1988), the disclosure of which is incorporated herein by reference in its entirety. The particular Fick technique algorithms used to process the measurements provided by the cardiac output monitor of the present invention are implemented in software; thus, any of a variety of techniques can be performed with the same apparatus simply by running different software on the processor. Moreover, software corresponding to a number of different Fick techniques can be stored in a memory of the cardiac output monitor, allowing the clinician to select a particular Fick technique that is desired or particularly well-suited to the clinical situation, or to determine cardiac output from more than one Fick technique.

Having described preferred embodiments of a new and improved method and apparatus for non-invasively determining cardiac output and pulmonary function using respired gas analysis techniques and physiological modeling, it is believed that other modifications, variations and changes will be suggested to those skilled in the art in view of the teachings set forth herein. It is therefore to be understood that all such variations, modifications and changes are believed to fall within the scope of the present invention as defined by the appended claims. Although specific terms are employed herein, they are used in a generic and descriptive sense only and not for purposes of limitation.

What is claimed is:

1. A cardiac output monitoring system for non-invasively determining cardiac output on a breath-by-breath basis from respiratory gasses of a subject, comprising:

a flowmeter configured to receive a respiratory gas stream and determine respired flow rates at selected time intervals during a respiratory cycle, wherein the respiratory cycle includes inhalation of a gas stream into the subject's lungs and exhalation of the gas stream out of the subject's lungs, so as to provide flow rate data as a function of time over the respiratory cycle;

a gas analyzer configured to simultaneously determine individual concentrations of a plurality of constituents in the gas stream in real time at selected time intervals during the respiratory cycle so as to provide concentration data for each constituent as a function of time over the respiratory cycle; and a processor coupled to the flowmeter and the gas analyzer and configured to determine cardiac output during the respiratory cycle utilizing flow rate data obtained from the flowmeter and the concentration data obtained from the gas analyzer.

2. The cardiac output monitoring system of claim 1, wherein the processor determines cardiac output by applying the Fick principle.

3. The cardiac output monitoring system of claim 1, wherein the processor is configured to continuously monitor the cardiac output of the subject by utilizing flow rate data obtained from the flowmeter and concentration data obtained from the gas analyzer during a plurality of respiratory cycles.

4. The cardiac output monitoring system of claim 2, wherein the processor determines the exchange rate between alveolar gas and pulmonary blood flow of the subject for at least one constituent utilizing the flow rate data obtained from the flowmeter and the concentration data obtained from the gas analyzer for the at least one constituent.

5. The cardiac output monitoring system of claim 2, wherein the gas analyzer is further configured to simultaneously determine individual partial pressures of the plurality of constituents in the gas stream so as to provide partial pressure data for each constituent as a function of time over the respiratory cycle.

6. The cardiac output monitoring system of claim 5, wherein the processor utilizes an algorithm incorporating the effects of deadspace and shunts in the subject's lungs to determine cardiac output.

7. The cardiac output monitoring system of claim 5, wherein the algorithm iteratively applies a physiological model to determine cardiac output.

8. The cardiac output monitoring system of claim 7, wherein the processor is further configured to determine at least one of shunt amount and deadspace for the subject utilizing the algorithm.

9. A method of determining a subject's cardiac output on a breath-by-breath basis, the method comprising:

(a) measuring a flow rate of a respiratory gas stream of the subject at a plurality of selected time intervals during a respiratory cycle, wherein the respiratory cycle includes inhalation of the gas stream into the subject's lungs and exhalation of the gas stream out of the subject's lungs, so as to obtain flow rate data as a function of time over the respiratory cycle;

(b) measuring a concentration of at least one constituent within the gas stream in real time at the plurality of selected time intervals during the respiratory cycle so as to obtain concentration data of the at least one constituent in the gas stream as a function of time over the respiratory cycle; and (c) calculating a cardiac output for the patient based upon the measured flow rate data of the gas stream and the measured concentration data of the at least one constituent.

10. The method of claim 9, wherein step (c) comprises:

(c1) determining an exchange rate of the at least one constituent between alveolar gas in the patient's lungs and the subject's pulmonary blood flow during the respiratory cycle;

(c2) determining an arteriovenous concentration difference of the at least one constituent during the respiratory cycle; and (c3) calculating the cardiac output based upon a ratio of the exchange rate of the at least one constituent to the arteriovenous concentration difference of the at least one constituent.

11. The method of claim 10, wherein step (c1) comprises determining the exchange rate of the at least one constituent by multiplying the measured flow rate data by the measured concentration data of the at least one constituent and integrating the product over the plurality of selected time intervals.

12. The method of claim 10, wherein step (b) includes measuring a partial pressure of the at least one constituent in the gas stream at the plurality of selected time intervals during the respiratory cycle, and the arteriovenous concentration difference for the at least one constituent is correlated with a measured partial pressure value of the at least one constituent within the gas stream at an end tidal expiration of the respiratory cycle.

13. The method of claim 9, wherein the gas stream includes a bolus of an indicator gas injected into the gas stream prior to step (a), and the at least one constituent includes the indicator gas.

14. The method of claim 13, wherein the indicator gas is selected from the group consisting of nitrogen, nitrous oxide, sevoflurane, desflurane and helium.

15. The method of claim 9, wherein the at least one constituent includes oxygen and carbon dioxide, and each concentration of oxygen is measured simultaneously with each concentration of carbon dioxide during the respiratory cycle.

16. The method of claim 15, wherein step (b) includes measuring a partial pressure of oxygen and a partial pressure of carbon dioxide in the gas stream at the plurality of selected time intervals during the respiratory cycle so as to obtain partial pressure data for oxygen and carbon dioxide in the gas stream as a function of time over the respiratory cycle.

17. The method of claim 16, wherein step (c) includes utilizing an algorithm to determine at least one of an amount of deadspace and an amount of shunt associated with the subject's lungs, and modifying the calculation of the cardiac output based upon the determination.

18. The method of claim 17, wherein the algorithm iteratively applies a physiological model in order to determine cardiac output.

19. The method of claim 17, wherein the algorithm comprises the following iterative steps:

(c1) assigning partial pressure values of the measured carbon dioxide partial pressure data, including a value representing the carbon dioxide alveolar partial pressure, to a converging data set;

(c2) estimating the deadspace in the subject's lungs based upon the converging data set of carbon dioxide partial pressure values;

(c3) estimating a cardiac output value based upon the measured flow rate data, the measured concentration data for oxygen and carbon dioxide, the estimated deadspace value and an estimated shunt adjustment value;

(c4) estimating new values for the converging data set, including a new value for the carbon dioxide alveolar partial pressure, based upon a gas uptake simulation model for the patient, wherein the gas uptake simulation model incorporates a plurality of physiological factors including oxygen consumption, estimated deadspace and shunt values and estimated cardiac output; and (c5) repeating steps (c2)–(c4) until the converging data set converges with the measured carbon dioxide partial pressure data within a selected range of values, such that a final estimated cardiac output calculated in step (c3) represents the cardiac output of the subject.

20. The method of claim 9, wherein the method further comprises:

(d) repeating steps (a)–(c) so as to continuously monitor the subject's cardiac output during a plurality of respiratory cycles.

21. A method of determining a subject's cardiac output on a breath-by-breath basis, the method comprising:

(a) measuring an entrance flow rate of a respiratory gas stream of the subject at a first plurality of selected time intervals so as to obtain entrance flow rate data as a function of time during an inhalation of the gas stream into the subject's lungs;

(b) measuring an exit flow rate of the gas stream of the subject at a second plurality of selected time intervals so as to obtain exit flow rate data as a function of time during an exhalation of the gas stream out of the subject's lungs;

(c) measuring a concentration of at least one constituent within the gas stream in real time at the first and second pluralities of selected time intervals so as to obtain concentration data of the at least one constituent in the gas stream as a function of time during the inhalation of the gas stream into the subject's lungs and the exhalation of the gas stream out of the subject's lungs; and (d) calculating a cardiac output for the subject based upon the measured entrance and exit flow rate data of the gas stream and the measured concentration data of the at least one constituent.

* * * * *